(12) United States Patent
Molaei et al.

(10) Patent No.: US 8,152,841 B2
(45) Date of Patent: Apr. 10, 2012

(54) MEDICAL DEVICES INCLUDING METALLIC FILMS

(75) Inventors: Masoud Molaei, Mountain View, CA (US); William S. Henry, Oakland, CA (US); Gregory D. Chin, San Leandro, CA (US); Robert Z. Obara, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 75 days.

(21) Appl. No.: 12/766,076

(22) Filed: Apr. 23, 2010

(65) Prior Publication Data

US 2010/0204784 A1 Aug. 12, 2010

Related U.S. Application Data

(63) Continuation of application No. 11/130,534, filed on May 16, 2005, now Pat. No. 7,854,760.

(51) Int. Cl.
*A61F 2/82* (2006.01)
(52) U.S. Cl. ..................................... 623/1.15
(58) Field of Classification Search ......... 623/1.11–1.48
See application file for complete search history.

(56) References Cited

U.S. PATENT DOCUMENTS

| | | |
|---|---|---|
| 4,793,348 A | 12/1988 | Palmaz |
| 4,864,824 A | 9/1989 | Gabriel et al. |
| 5,035,706 A | 7/1991 | Giantureo et al. |
| 5,061,914 A | 10/1991 | Busch et al. |
| 5,085,535 A | 2/1992 | Solberg et al. |
| 5,119,555 A | 6/1992 | Johnson |
| 5,245,738 A | 9/1993 | Johnson |
| 5,302,261 A | 4/1994 | LeRoy et al. |
| 5,306,294 A | 4/1994 | Winston et al. |
| 5,325,880 A | 7/1994 | Johnson et al. |
| 5,382,261 A | 1/1995 | Palmaz |
| 5,405,378 A | 4/1995 | Strecker et al. |
| 5,441,515 A | 8/1995 | Khosravi et al. |
| 5,518,680 A | 5/1996 | Cima et al. |
| 5,554,182 A | 9/1996 | Dinh et al. |
| 5,556,413 A | 9/1996 | Lam |
| 5,607,466 A | 3/1997 | Imbert et al. |
| 5,619,177 A | 4/1997 | Johnson et al. |
| 5,656,036 A | 8/1997 | Palmaz |
| 5,667,523 A | 9/1997 | Bynon et al. |
| 5,674,242 A | 10/1997 | Phan et al. |
| 5,676,697 A | 10/1997 | McDonald |
| 5,728,150 A | 3/1998 | McDonald et al. |

(Continued)

FOREIGN PATENT DOCUMENTS

EP 0 472 731 8/1991

(Continued)

OTHER PUBLICATIONS

Partial International Search Report for PCT/US2006/019126.

(Continued)

*Primary Examiner* — Suzette J Gherbi
(74) *Attorney, Agent, or Firm* — Bingham McCutchen LLP

(57) ABSTRACT

Medical devices, such as endoprostheses, and methods of making the devices are disclosed. The medical device can include a composite cover formed of a deposited metallic film and one or more polymer layers. The polymer layers contribute to mechanical or biological properties of the endoprosthesis.

21 Claims, 14 Drawing Sheets

U.S. PATENT DOCUMENTS

| | | | |
|---|---|---|---|
| 5,755,734 A | 5/1998 | Richter et al. |
| 5,800,517 A | 9/1998 | Anderson et al. |
| 5,817,102 A | 10/1998 | Johnson et al. |
| 5,824,042 A | 10/1998 | Lombardi et al. |
| 5,824,049 A | 10/1998 | Ragheb et al. |
| 5,824,054 A | 10/1998 | Khosravi et al. |
| RE35,988 E | 12/1998 | Winston et al. |
| 5,843,158 A | 12/1998 | Lenker et al. |
| 5,843,164 A | 12/1998 | Frantzen et al. |
| 5,843,289 A | 12/1998 | Lee et al. |
| 5,849,206 A | 12/1998 | Amon et al. |
| 5,860,998 A | 1/1999 | Robinson et al. |
| 5,865,723 A | 2/1999 | Love |
| 5,882,444 A | 3/1999 | Flomenblit et al. |
| 5,888,734 A | 3/1999 | Cremer et al. |
| 5,897,911 A | 4/1999 | Loeffler |
| 5,903,099 A | 5/1999 | Johnson et al. |
| 5,938,697 A | 8/1999 | Killion et al. |
| 5,941,249 A | 8/1999 | Maynard |
| 5,957,929 A | 9/1999 | Brenneman |
| 5,984,963 A | 11/1999 | Ryan et al. |
| 6,007,573 A | 12/1999 | Wallace et al. |
| 6,015,431 A | 1/2000 | Thornton et al. |
| 6,015,433 A | 1/2000 | Roth |
| 6,017,977 A | 1/2000 | Evans et al. |
| 6,036,725 A | 3/2000 | Avellanet |
| 6,043,451 A | 3/2000 | Julien et al. |
| 6,048,622 A | 4/2000 | Hagood et al. |
| 6,059,766 A | 5/2000 | Greff |
| 6,077,298 A | 6/2000 | Tu et al. |
| 6,096,175 A | 8/2000 | Roth |
| 6,099,561 A | 8/2000 | Alt |
| 6,107,004 A | 8/2000 | Donadio, III |
| 6,120,535 A | 9/2000 | McDonald et al. |
| 6,132,460 A | 10/2000 | Thompson |
| 6,133,547 A | 10/2000 | Maynard |
| 6,139,564 A | 10/2000 | Teoh |
| 6,143,022 A | 11/2000 | Shull et al. |
| 6,159,239 A | 12/2000 | Greenhalgh |
| 6,174,330 B1 | 1/2001 | Stinson |
| 6,190,404 B1 | 2/2001 | Palmaz et al. |
| 6,206,911 B1 | 3/2001 | Milo |
| 6,224,627 B1 | 5/2001 | Armstrong et al. |
| 6,224,630 B1 | 5/2001 | Bao et al. |
| 6,245,104 B1 | 6/2001 | Alt |
| 6,254,628 B1 | 7/2001 | Wallace et al. |
| 6,258,117 B1 | 7/2001 | Camrud et al. |
| 6,290,720 B1 | 9/2001 | Khosravi et al. |
| 6,303,100 B1 | 10/2001 | Ricci et al. |
| 6,315,788 B1 | 11/2001 | Roby |
| 6,315,794 B1 | 11/2001 | Richter |
| 6,355,055 B1 | 3/2002 | Waksman et al. |
| 6,379,383 B1 | 4/2002 | Palmaz et al. |
| 6,398,803 B1 | 6/2002 | Layne et al. |
| 6,406,487 B2 | 6/2002 | Brenneman |
| 6,406,490 B1 | 6/2002 | Roth |
| 6,409,749 B1 | 6/2002 | Maynard |
| 6,428,569 B1 | 8/2002 | Brown |
| 6,447,478 B1 | 9/2002 | Maynard |
| 6,454,738 B1 | 9/2002 | Tran et al. |
| 6,458,152 B1 | 10/2002 | Khosravi et al. |
| 6,458,153 B1 | 10/2002 | Bailey et al. |
| 6,471,980 B2 | 10/2002 | Sirhan et al. |
| 6,485,510 B1 | 11/2002 | Camrud et al. |
| 6,506,211 B1 | 1/2003 | Skubitz et al. |
| 6,520,984 B1 | 2/2003 | Garrison et al. |
| 6,527,919 B1 | 3/2003 | Roth |
| 6,533,905 B2 | 3/2003 | Johnson et al. |
| 6,537,310 B1 | 3/2003 | Palmaz et al. |
| 6,605,111 B2 | 8/2003 | Bose et al. |
| 6,614,570 B2 | 9/2003 | Johnson et al. |
| 6,618,921 B1 | 9/2003 | Thornton |
| 6,620,192 B1 | 9/2003 | Jalisi |
| 6,620,634 B2 | 9/2003 | Johnson et al. |
| 6,624,730 B2 | 9/2003 | Johnson et al. |
| 6,629,993 B2 | 10/2003 | Voinov |
| 6,632,240 B2 | 10/2003 | Khosravi et al. |
| 6,638,301 B1 | 10/2003 | Chandrasekaran et al. |
| 6,666,882 B1 | 12/2003 | Bose et al. |
| 6,669,719 B2 | 12/2003 | Wallace et al. |
| 6,669,721 B1 | 12/2003 | Bose et al. |
| 6,669,795 B2 | 12/2003 | Johnson et al. |
| 6,673,102 B1 | 1/2004 | Vonesh et al. |
| 6,676,987 B2 | 1/2004 | Zhong et al. |
| 6,695,865 B2 | 2/2004 | Boyle et al. |
| 6,699,278 B2 | 3/2004 | Fischell et al. |
| 6,699,279 B2 | 3/2004 | Stevens et al. |
| 6,746,478 B2 | 6/2004 | Jayaraman |
| 6,752,826 B2 | 6/2004 | Holloway et al. |
| 6,767,418 B1 | 7/2004 | Zhang et al. |
| 6,776,795 B2 | 8/2004 | Pelton |
| 6,820,676 B2 | 11/2004 | Palmaz et al. |
| 6,849,085 B2 | 2/2005 | Marton |
| 6,936,066 B2 | 8/2005 | Palmaz et al. |
| 6,953,560 B1 | 10/2005 | Castro et al. |
| 7,105,018 B1 | 9/2006 | Yip et al. |
| 7,279,175 B2 | 10/2007 | Chen et al. |
| 7,410,497 B2 | 8/2008 | Hastings et al. |
| 7,947,071 B2 * | 5/2011 | Schmid et al. ............... 623/1.22 |
| 2001/0001834 A1 | 5/2001 | Palmaz et al. |
| 2001/0032013 A1 | 10/2001 | Marton |
| 2001/0039449 A1 | 11/2001 | Johnson et al. |
| 2001/0044647 A1 | 11/2001 | Pinchuk et al. |
| 2002/0007958 A1 | 1/2002 | Rivelli et al. |
| 2002/0017503 A1 | 2/2002 | Banas et al. |
| 2002/0019662 A1 | 2/2002 | Brauckman et al. |
| 2002/0035774 A1 | 3/2002 | Austin |
| 2002/0042645 A1 | 4/2002 | Shannon |
| 2002/0046783 A1 | 4/2002 | Johnson et al. |
| 2002/0142119 A1 | 10/2002 | Seward et al. |
| 2002/0151965 A1 | 10/2002 | Roth |
| 2002/0161342 A1 | 10/2002 | Rivelli, Jr. et al. |
| 2002/0162605 A1 | 11/2002 | Horton, Jr. et al. |
| 2002/0165576 A1 | 11/2002 | Boyle et al. |
| 2002/0165600 A1 | 11/2002 | Banas et al. |
| 2002/0173809 A1 | 11/2002 | Fleischman et al. |
| 2002/0187288 A1 | 12/2002 | Lim et al. |
| 2002/0193869 A1 | 12/2002 | Dang |
| 2002/0195579 A1 | 12/2002 | Johnson |
| 2002/0198584 A1 * | 12/2002 | Unsworth et al. ............ 623/1.11 |
| 2003/0002994 A1 | 1/2003 | Johnson et al. |
| 2003/0004567 A1 | 1/2003 | Boyle et al. |
| 2003/0018354 A1 | 1/2003 | Roth et al. |
| 2003/0023303 A1 | 1/2003 | Palmaz et al. |
| 2003/0040791 A1 | 2/2003 | Oktay |
| 2003/0050691 A1 | 3/2003 | Shifrin et al. |
| 2003/0059640 A1 | 3/2003 | Marton et al. |
| 2003/0060782 A1 | 3/2003 | Bose et al. |
| 2003/0074049 A1 | 4/2003 | Hoganson et al. |
| 2003/0078649 A1 | 4/2003 | Camrud et al. |
| 2003/0083731 A1 | 5/2003 | Kramer et al. |
| 2003/0127318 A1 | 7/2003 | Johnson et al. |
| 2003/0130718 A1 | 7/2003 | Palmas et al. |
| 2003/0130721 A1 | 7/2003 | Martin et al. |
| 2003/0139797 A1 | 7/2003 | Johnson et al. |
| 2003/0153971 A1 | 8/2003 | Chandrasekaran |
| 2003/0159920 A1 | 8/2003 | Roth |
| 2003/0185895 A1 | 10/2003 | Lanphere et al. |
| 2003/0187495 A1 | 10/2003 | Cully et al. |
| 2003/0212430 A1 | 11/2003 | Bose et al. |
| 2004/0006381 A1 | 1/2004 | Sequin et al. |
| 2004/0014253 A1 | 1/2004 | Gupta et al. |
| 2004/0030377 A1 | 2/2004 | Dubson et al. |
| 2004/0034408 A1 | 2/2004 | Majercak et al. |
| 2004/0054399 A1 | 3/2004 | Roth |
| 2004/0054406 A1 | 3/2004 | Dubson et al. |
| 2004/0059410 A1 | 3/2004 | Cox |
| 2004/0107004 A1 | 6/2004 | Levine et al. |
| 2004/0143317 A1 | 7/2004 | Stinson et al. |
| 2004/0199239 A1 | 10/2004 | Austin et al. |
| 2004/0225350 A1 * | 11/2004 | Shanley .................. 623/1.16 |
| 2004/0254520 A1 | 12/2004 | Porteous et al. |
| 2005/0004653 A1 | 1/2005 | Gerberding et al. |
| 2005/0010275 A1 | 1/2005 | Sahatjian et al. |
| 2005/0033399 A1 | 2/2005 | Richter |
| 2005/0165468 A1 | 7/2005 | Marton |
| 2005/0165469 A1 * | 7/2005 | Hogendijk ................ 623/1.15 |

| | | | |
|---|---|---|---|
| 2005/0197687 A1 | 9/2005 | Molaei et al. | |
| 2005/0197689 A1 | 9/2005 | Molaei | |
| 2005/0197690 A1 | 9/2005 | Molaei et al. | |
| 2006/0069428 A1* | 3/2006 | Feller, III | 623/1.44 |
| 2006/0100659 A1 | 5/2006 | Dinh et al. | |
| 2006/0115514 A1 | 6/2006 | Gengrinovitch | |
| 2006/0122691 A1 | 6/2006 | Richter | |
| 2006/0142838 A1 | 6/2006 | Molaei et al. | |
| 2006/0142842 A1 | 6/2006 | Molaei et al. | |
| 2006/0142845 A1 | 6/2006 | Molaei et al. | |
| 2006/0142851 A1 | 6/2006 | Molaei et al. | |
| 2006/0147492 A1 | 7/2006 | Hunter et al. | |
| 2006/0184231 A1 | 8/2006 | Rucker | |
| 2006/0259131 A1 | 11/2006 | Molaei et al. | |
| 2006/0271158 A1* | 11/2006 | Olson | 623/1.15 |
| 2007/0016283 A1* | 1/2007 | Greenhalgh et al. | 623/1.15 |
| 2007/0073385 A1 | 3/2007 | Schaeffer et al. | |
| 2007/0112411 A1 | 5/2007 | Obermiller et al. | |
| 2007/0250156 A1 | 10/2007 | Palmaz | |
| 2008/0027388 A1 | 1/2008 | Banas et al. | |
| 2008/0221665 A1* | 9/2008 | Peckham et al. | 623/1.22 |
| 2009/0132022 A1* | 5/2009 | Banas | 623/1.13 |
| 2009/0187240 A1 | 7/2009 | Clerc et al. | |
| 2010/0030320 A1 | 2/2010 | Feller, III | |
| 2011/0054590 A1* | 3/2011 | Leopold et al. | 623/1.15 |

FOREIGN PATENT DOCUMENTS

| | | |
|---|---|---|
| EP | 0 792 627 | 9/1997 |
| EP | 1604697 | 12/2005 |
| EP | 1 725 186 | 11/2006 |
| EP | 1 725 187 | 11/2006 |
| EP | 1 725 188 | 11/2006 |
| GB | 2 125 442 | 3/1984 |
| JP | 2003-102849 | 8/2003 |
| JP | 2007/502069 | 9/2007 |
| JP | 2007/526098 | 9/2007 |
| JP | 2007/526099 | 9/2007 |
| WO | 96/06814 | 3/1996 |
| WO | 98/53362 | 11/1998 |
| WO | 99/02092 | 1/1999 |
| WO | 99/60267 | 12/1999 |
| WO | 99/62432 | 12/1999 |
| WO | 00/62711 | 10/2000 |
| WO | 01/21097 | 3/2001 |
| WO | 01/53559 | 7/2001 |
| WO | 01/87371 | 11/2001 |
| WO | 01/89420 | 11/2001 |
| WO | 01/91823 | 12/2001 |
| WO | 01/95697 | 12/2001 |
| WO | 02/38080 | 5/2002 |
| WO | 02/38086 | 5/2002 |
| WO | 02/34163 | 6/2002 |
| WO | 02/060506 | 8/2002 |
| WO | 03/003943 | 1/2003 |
| WO | 03/011363 | 2/2003 |
| WO | 03/013337 | 2/2003 |
| WO | 03/015840 | 2/2003 |
| WO | 03/018100 | 3/2003 |
| WO | 03/075793 | 9/2003 |
| WO | 03/075799 | 9/2003 |
| WO | 03/099161 A2 | 12/2003 |
| WO | 2004/002370 | 1/2004 |
| WO | 2004/008504 | 1/2004 |
| WO | 2004/028340 | 4/2004 |
| WO | 2005/084583 | 9/2005 |
| WO | 2005/084584 | 9/2005 |
| WO | 2005/084585 | 9/2005 |
| WO | 2006/125022 | 4/2006 |
| WO | 2006/071215 | 7/2006 |
| WO | 2006/071242 | 7/2006 |
| WO | 2006/071243 | 7/2006 |
| WO | 2006/071244 | 7/2006 |
| WO | 2006/071245 | 7/2006 |

OTHER PUBLICATIONS

Dieter, George, *Mechanical Metallurgy*, Singapore, McGraw-Hill Book Co., 10$^{th}$ Printing 1984, pp. 111-117, 142-145, and 234-237. TA405.D53.

Freiherr, Greg, "Shape-Memory Alloys Offer Untapped", Medical Device & Diagnostic Industry Magazine, Mar. 1998, 5 pages [retrieved on Jun. 30, 2004].

Fu et al., "TiNi-based thin films in MEMS applications: a review", Sensors and Actuators, Article in Press, Elsevier, Feb. 2004, 14 pages.

Gertner et al., "Drug Delivery from Electrochemically Deposited Thin Metal Films", Electrochemical and Sold-State Letter, 6 (4) J4-J6, 2003.

Gertner et al., "Electrochemistry and Medical Devices: Friend or Foe?", The Electrochemical Society Interface, Fall 2003, pp. 20-24.

Gupta et al., "*Nitinol Thin Film Three-Dimensional Devices—Fabrication and Applications*", http://www.tinialloy.com/pdf/smst.pdf, Sep. 7, 2003 [retrieved Dec. 1, 2004].

He et al., "$CO_2$ laser annealing of sputtering deposited NiTi shape memory thin films", Journal of Micromechanics and Microengineering, May 20, 2004, pp. 950-956.

Kaczmarek, S. M., "Pulsed laser deposition—today and tomorrow", STL'96, Proc. SPIE, vol. 3187, 1997, pp. 129-134.

Krebs et al., "Pulsed Laser Deposition (PLD)—a Versatile Thin Film Technique", Advances in Solid State Physics 2003, 43, 505-517.

Nakayama et al., "Fabrication of micropored elastomeric film-covered stents and acute-phase performances", Journal of Biomedical Mateirals Research Part A, vol. 64A, Issue 1, Sep. 30, 2002, pp. 52-61.

*Neocera, Inc. Brochure—Pulsed Laser Deposition*, www.neocera.com [retrieved Dec. 1, 2004].

Padhi et al., "Planarization of Copper Thin Films by Electropolishing in Phosphoric Acid for ULSI Application", Journal of Electrochemical Society, vol. 150, 2003, pp. G10-G14.

Pelleiter et al., "Effect of high energy argon implantation into NiTi shape memory alloy", Surface and Coatings Technology, 158-159, 2002, pp. 301-308.

Ren et al., "Carbon nitride materials synthesized by Ion-assisted pulsed laser deposition", RIKEN Review No. 43, Jan. 2002, pp. 41-44.

Schetky et al., "Issues in the Further Development of Nitinol Properties and Processing for Medical Device Application", Proceedings, ASM Materials & Processes for Medical Devices Conference, Anaheim, in press, 2003, 6 pages.

Shabalovskaya et al., "Comparative performances of Nitinol surfaces in protein adsorption and platelet adhesion—Preliminary results", Institute for Physical Research and Technology, Ames Laboratory, Ames, IA University of Washington, Seattle WA Memry Corporation, Bethel CT, 2004, 10 pages.

Stoeckel et al., "A survey of stent designs", Min Invas Ther & Allied Technol, 11(4), 2002, pp. 137-147.

International Search Report from related International Application No. PCT/US2005/007282 mailed Jul. 5, 2005, 15 pages.

International Search Report from related International Application No. PCT/US2005/006993 mailed Aug. 2, 2005, 21 pages.

International Search Report from related International Application No. PCT/US2005/007161 mailed Jul. 28, 2005, 45 pages.

International Search Report from related International Application No. PCT/US2005/007173 mailed Dec. 6, 2005, 19 pages.

International Search Report from related International Application No. PCT/US2005/007164 mailed Jul. 5, 2005, 13 pages.

International Search Report from related International Application No. PCT/US2005/007162 mailed Oct. 4, 2005, 16 pages.

International Search Report from related International Application No. PCT/US2005/006895 mailed Mar. 2, 2005, 16 pages.

* cited by examiner

MEDICAL DEVICES INCLUDING METALLIC FILMS

CROSS-REFERENCE TO RELATED APPLICATIONS

This application is a continuation application of and claims priority to U.S. application Ser. No. 11/130,534, filed on May 16, 2005, the entire contents of which are hereby incorporated by reference.

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen, e.g., adjacent the aneurysm. In some cases, the endoprosthesis is a stent coated with a bioabsorbable polymer to decrease its porosity in the short term.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some aspects, the invention relates to an endoprosthesis including first and second tubular frameworks spaced apart by a degradable central portion. The endoprosthesis defines an interior and an exterior. In certain embodiments, the tubular frameworks are configured to exert a radially expansive force against a body passage sufficient to retain the endoprosthesis with respect to the body passage. The degradable central portion can be configured to initially reduce a flow of blood between the interior and exterior of the endoprosthesis and, subsequent to deployment, degrade over time providing increased flow of blood between the interior and exterior of the endoprosthesis.

Another aspect of the invention relates to an endoprosthesis including a generally tubular deposited metallic film defining first and second ends and at least one fenestration located between the ends. In general, the at least one fenestration has an area sufficient to pass a microcatheter. A degradable layer initially obstructs the fenestration. Upon deployment of the endoprosthesis within a body passage, the degradable layer degrades thereby opening the fenestration to provide an area sufficient to allow passage of a microcatheter.

In some embodiments, the deposited metallic film includes nickel and titanium. The film can have a thickness of less than about 50 µm.

Another aspect of the invention relates to an endoprosthesis defining an interior and an exterior. The endoprosthesis includes a deposited metallic film having a plurality of fenestrations and a degradable polymer layer configured to reduce passage of liquid between the interior of the endoprosthesis and the exterior of the endoprosthesis along a path including the fenestrations. In some embodiments, the film has at least about 100 fenestrations. Upon deployment of the endoprosthesis within a body passage, the polymer layer typically degrades thereby allowing increased passage of fluid between the interior of the endoprosthesis and the exterior of the endoprosthesis along a path including the fenestrations.

Other aspects, features, and advantages of the invention will be apparent from the description of the preferred embodiments thereof and from the claims.

BRIEF DESCRIPTION OF THE FIGURES

FIG. 1b is a cross-section through the endoprosthesis of FIG. 1a.

FIG. 3b is a cross-section through the endoprosthesis of FIG. 3a.

FIG. 9b illustrates a radially compressed configuration of several plates of the endoprosthesis of FIG. 9a.

FIG. 9c illustrates a radially expanded configuration of several plates of the endoprosthesis of FIG. 9a.

DETAILED DESCRIPTION

Figure 1A:
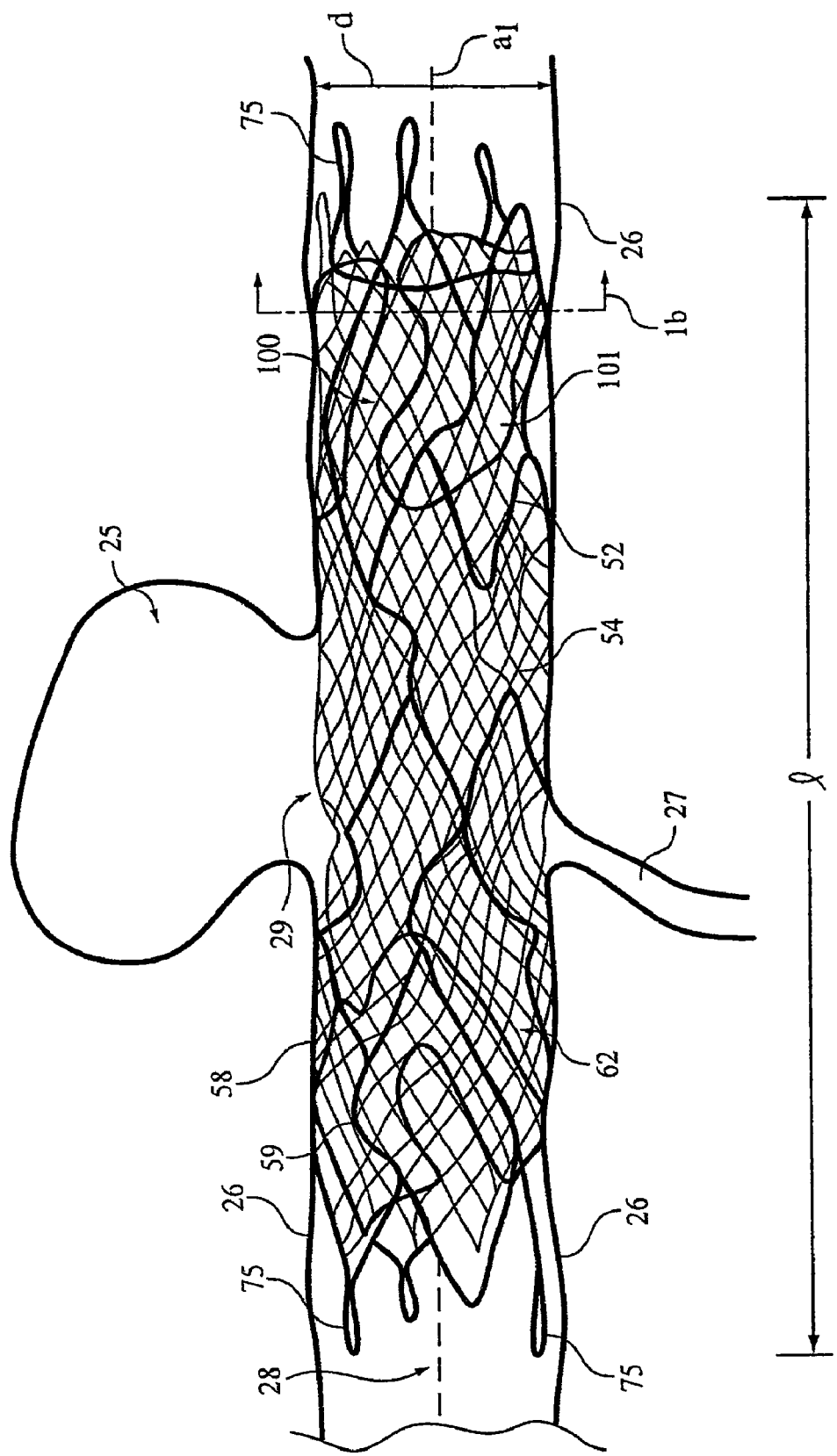
FIG. 1a is a side view of an endoprosthesis in the radially expanded state as deployed within a body passage adjacent an aneurysm. The endoprosthesis has a plurality of polymer layers.
Figure 1B:
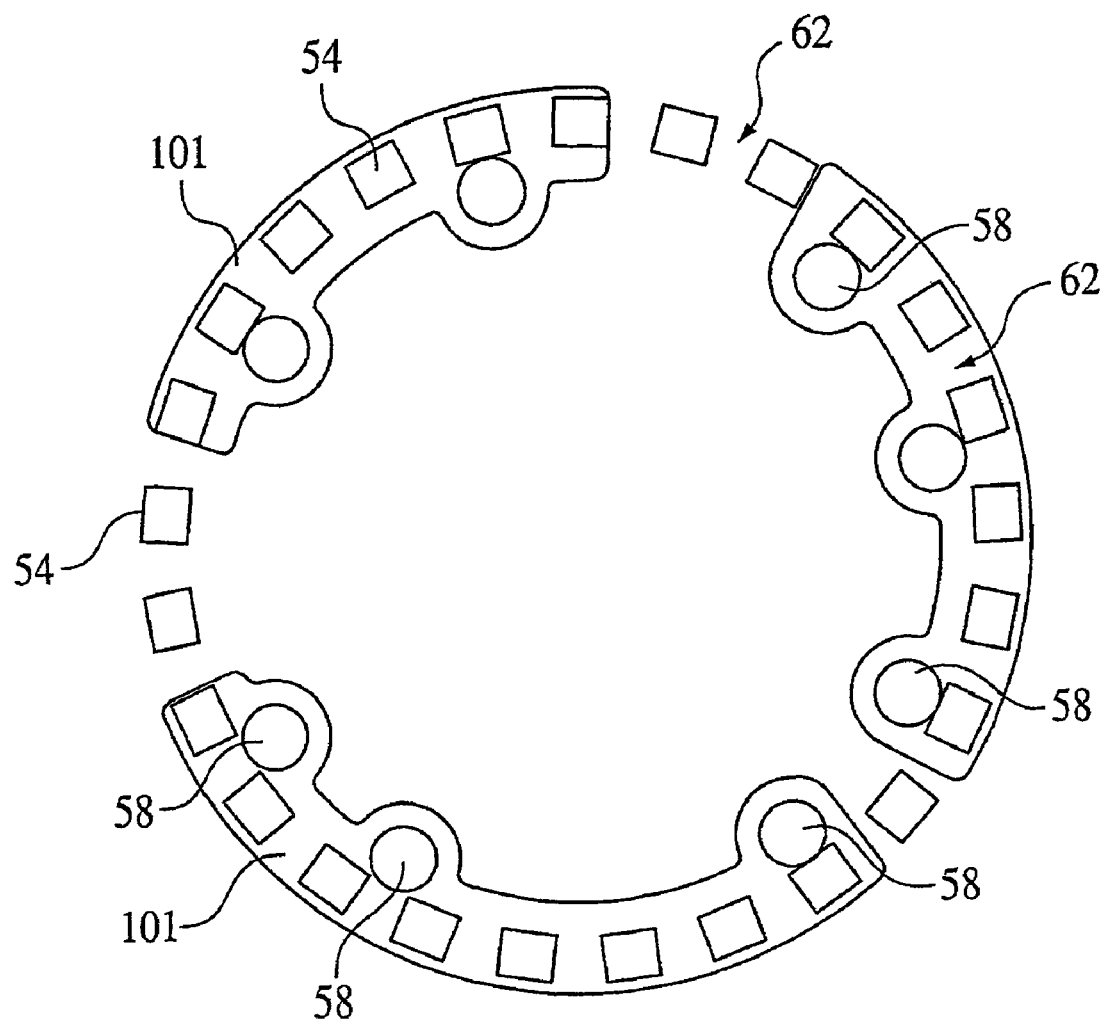

Referring to FIGS. 1a and 1b, an endoprosthesis 100 is deployed within a body passage, e.g., within a vessel weakened by an aneurysm, e.g., an aneurysm 25 of a vessel 26 of a human brain. Endoprosthesis 100 includes a framework, e.g., a stent body 52, covered by a tubular member or cover 54, which are secured to one another by polymer layers 101. The stent body provides a relatively rigid framework that secures the endoprosthesis at the treatment site. The framework defines relatively large openings or fenestrations that contribute to the mechanical properties of the stent. The cover 54 is relatively thin and flexible and includes smaller fenestrations that contribute to the mechanical properties of the cover 54 and can occlude the fenestrations of the stent.

The endoprosthesis 100 modifies an amount or velocity of blood passing between vessel 26 and aneurysm 25. For example, prosthesis 100 can be deployed to divert, reduce or block blood flow between vessel 26 and aneurysm 25. The endoprosthesis can also reduce blood flow between vessel 26 and a feeder vessel 27. If so deployed, prosthesis 100 may sufficiently reduce blood flow to allow clotting or other healing processes to take place within aneurysm 25 and/or opening 29. Tubular member 54 can provide a greater attenuation of the blood flow into the aneurysm 25 than stent body 52 alone. Endoprosthesis 100, however, can allow some flow to pass between vessel 26 and aneurysm 25 even while providing flow diversion and/or reduction in flow. Prosthesis 100 can also (or alternatively) allow blood to pass between vessel 26 containing the prosthesis and adjacent vessels, e.g., feeder vessel 27, while still providing reduced flow with respect to the aneurysm.

Figure 2A:
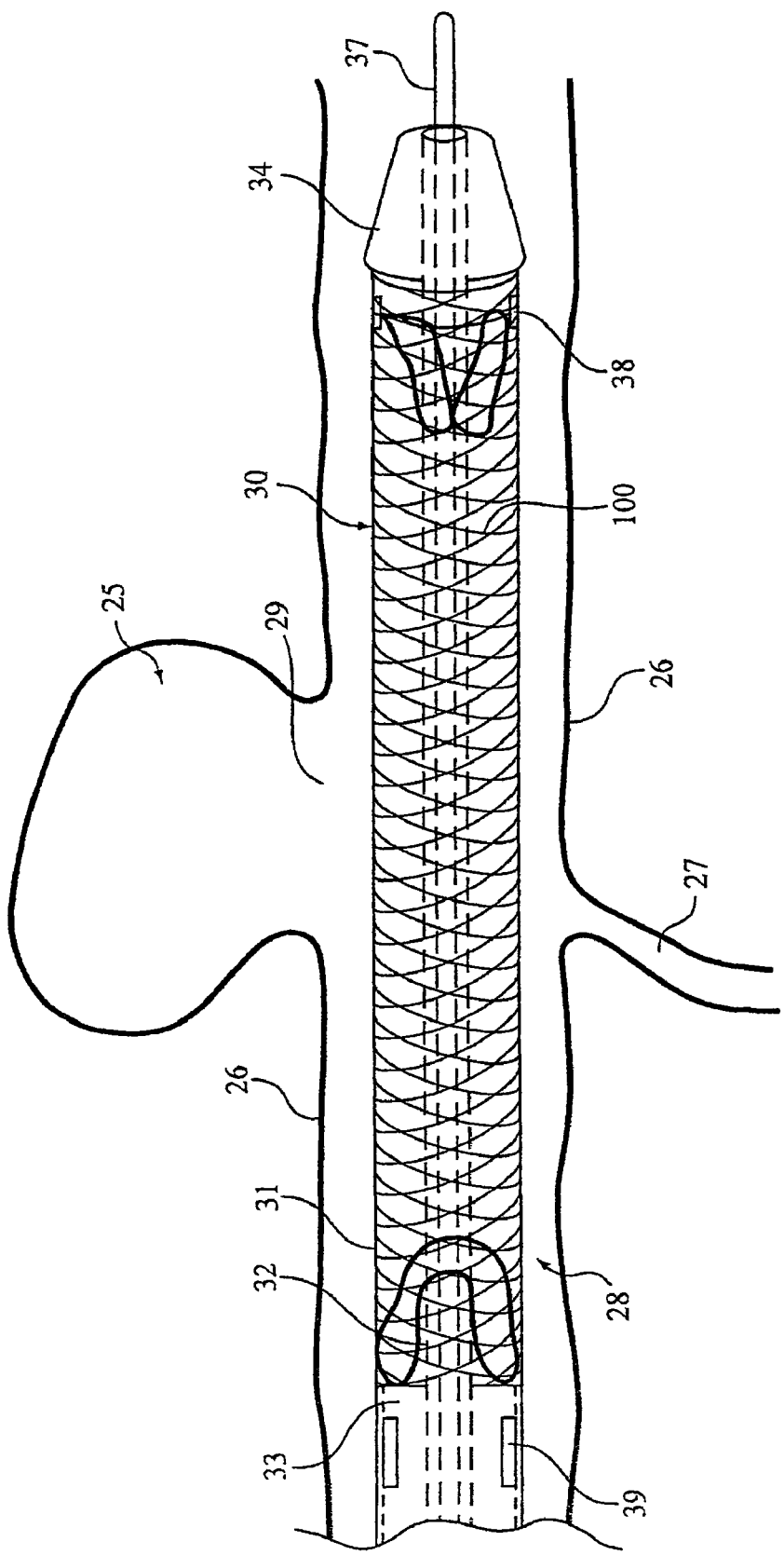
FIG. 2a is a side view of a distal portion of a deployment device prior to radial expansion of the endoprosthesis.
Figure 2B:
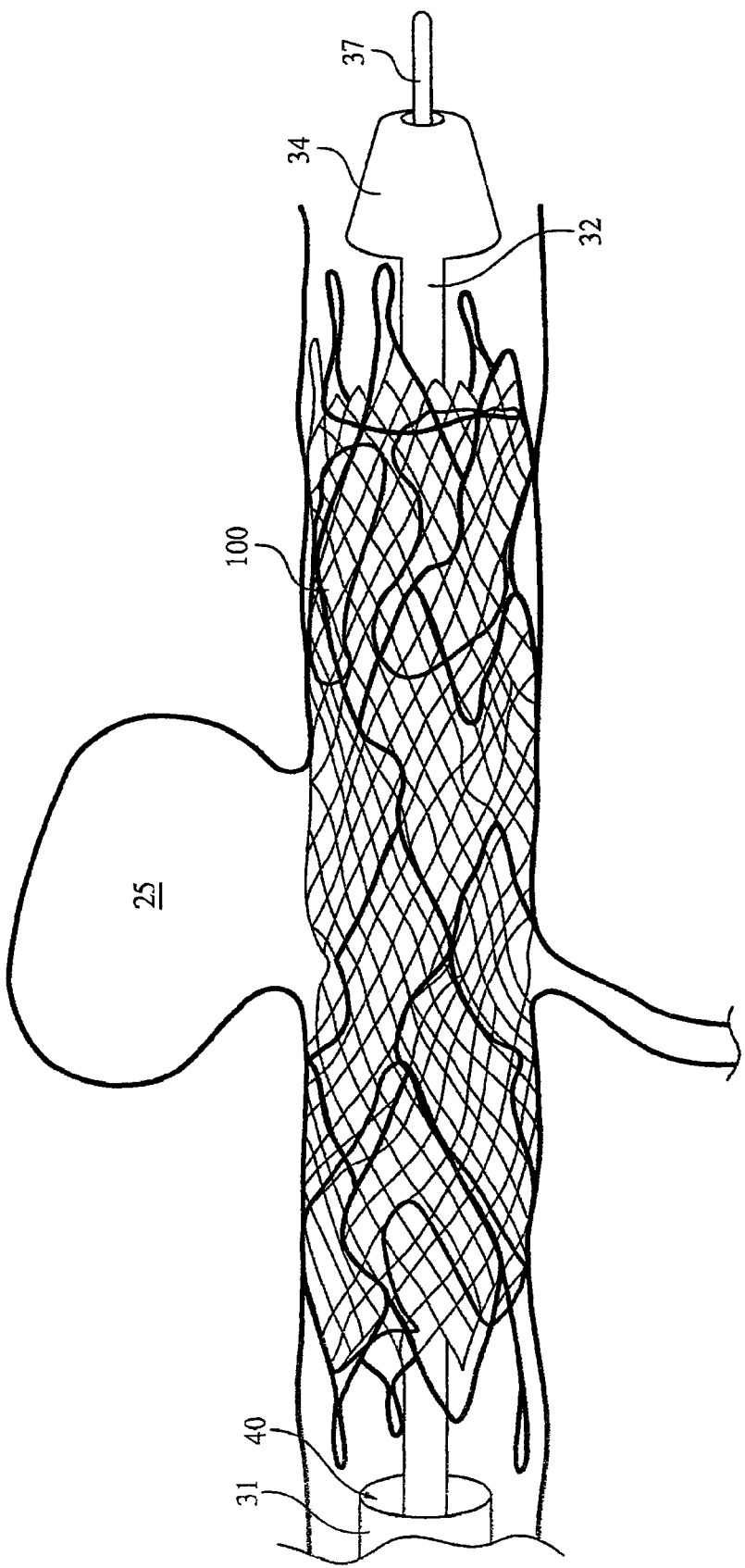
FIG. 2b is a side view of the distal portion of the deployment device subsequent to radial expansion of the endoprosthesis adjacent the aneurysm.

Referring to FIGS. 2a and 2b, endoprosthesis 100 is deployed to aneurysm 25 using a deployment device 30, such as a catheter that can be threaded through a tortuous anatomy. The device 30 includes a retractable outer sheath 31 and an inner catheter 32. Device 30 is introduced over a guide wire 37 extending along the interior 28 of vessel 26. During introduction, the endoprosthesis 100 is radially compacted between outer sheath 31 and inner catheter 32 adjacent a distal opening 40 of the outer sheath.

Referring particularly to FIG. 2b, the outer sheath 31 is retracted upon reaching the desired deployment site, e.g., aneurysm 25. In some embodiments, endoprosthesis 100 self-expands by its own internal elastic restoring force when the radially restraining outer sheath is retracted. Alternatively, or in combination with self-expansion, deployment of prosthesis 100 may include use of a balloon or other device to radially expand prosthesis 100 within vessel 26. After deploying the endoprosthesis, the inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures.

Upon expansion, the endoprosthesis assumes a shape and radial extent generally coextensive with an inner surface of the vessel 26, e.g., a tubular shape centered about a longitudinal axis a1 of the prosthesis (FIG. 1a). Depending upon the application, prosthesis 100 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 100 can have a length along axis a1 of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

The cover can be fixed to the stent by, e.g. fasteners. Attachment techniques include brazing, welding or attachment with a filament, rivets or grommets, or crimping, or adhesive. In some embodiments, the tubular member differs from a fabric at least in that the tubular member lacks fibers that can be pushed apart to receive a filament as by sewing a fabric. Accordingly, the fenestrations can be formed prior to the process of passing the filament through the tubular member. Fenestrations that receive the filaments can be formed by, e.g., etching, laser cutting, or a photolithographic process. Attachment techniques are described in U.S. Ser. No. 11/025,866, titled MEDICAL DEVICES INCLUDING METALLIC FILMS AND METHODS FOR MAKING SAME, filed Dec. 29, 2004 and incorporated herein by reference.

The cover is formed of a thin film that exhibits advantageous properties such as strength, toughness, and flexibility by selection of the composition of the film, processing techniques, and mechanical configuration. For example, in particular embodiments, the film is a vapor-deposited material composed of a nickel-titanium alloy having a strength additive, e.g. chromium. The film has a thickness of about 50 μm or less, e.g. about 4-35 μm, and includes fine fenestrations, which facilitate collapsing the film to small diameter for delivery into the body and expansion at the treatment site, while impeding blood access to the aneurysm. In some embodiments, the film has at least about 100 fenestrations, e.g., at least about 250 fenestrations. In particular embodiments, the film is processed to modify dislocations, which contribute to strength and toughness of the thin film.

Deposited materials, e.g., metallic films, are formed by depositing film constituents from a suspended state, e.g. in a vapor or a vacuum onto a surface. In embodiments, the constituents are suspended, e.g. by bombarding, heating or sputtering a bulk target. The suspended constituents deposit on a substrate to form the film. Deposited films can exhibit highly uniform thickness and microstructure in very thin films, e.g. about 50 μm or less, e.g. 4-35 μm. Deposition techniques include sputter deposition, pulsed laser deposition, ion beam deposition and plasma deposition. Suitable deposition processes are described in Busch et al. U.S. Pat. No. 5,061,914, Bose et al. U.S. Pat. No. 6,605,111, Johnston U.S. Pat. No. 6,533,905, and Gupta et al. U.S. 2004/0014253, the entire contents of all of which are hereby incorporated by reference.

In particular embodiments, the deposited film is an alloy that includes nickel and titanium, and a strength additive or additives, which modify a mechanical property, e.g., a hardness or elasticity, of the film. In particular embodiments, the film is a tertiary alloy that has substantially no other components besides nickel, titanium, and additive present in an amount greater than 1%, 0.5% or 0.1% or less than 20%, 10%, or 5% by weight of the film. The film may consist essentially of nickel, titanium, and chromium. In embodiments, the deposited film includes between 54 and 57 weight percent nickel with the balance composed essentially of titanium and chromium. In some embodiments, a ratio of a weight of chromium of the film to a combined weight of nickel, titanium, and chromium of the film is at least 0.001, at least 0.002 e.g., at least 0.0025. The ratio of the weight of chromium of the film to the combined weight of chromium, nickel, and titanium of the film can be 0.02 or less, 0.01 or less, e.g., 0.0075 or less. The ratio of the weight of chromium to the combined weight of chromium, nickel, and titanium of the film can be about 0.0025. In embodiments, the alloy exhibits superelastic or pseudo-elastic properties. Superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003.

A cover of deposited metal film contributes to desirable properties of an endoprosthesis. For example, as discussed above, cover 54 contributes to a flow diversion or reduction function. In some embodiments, a configuration and mechanical properties of the metallic film enhance the ability of the cover to withstand significant radial compression during deployment yet provide desirable properties in situ. An endoprosthesis can also include polymer layers, which, alone or in cooperation with a cover, contribute to properties of the endoprosthesis. Some polymer layers provide a mechanical function such as by securing a cover and stent body together or modifying surface properties of a metallic film, e.g., a lubricity or a roughness thereof. In embodiments, a polymer modifies a radial force exerted by the endoprosthesis against a body passage. Some polymers lend biological functionality to the endoprosthesis. For example, a polymer may improve biocompatibility, enhance cell growth, or provide a pharmacological function, e.g., release of a therapeutic agent. In some embodiments, a polymer of an endoprosthesis degrades with time modifying mechanical and/or biological properties of the endoprosthesis. Embodiments of endoprostheses including covers having a metallic film are now described.

Returning to FIGS. 1a and 1b, polymer layers 101 have a pattern that generally aligns with portions of the stent body, e.g., framework members 58,59 of the stent body. FIG. 1b shows that polymer layers 101 envelope members 58 and cover 54. A securing function is provided by mechanical properties of the polymer, which prevent the stent body and cover from tearing completely apart. Despite securing the stent body and tubular member, polymer layer 101 can allow some relative movement between the stent body and tubular member. In embodiments, relative movement occurs during radial compression and expansion and provides tolerance for some differential length changes, e.g., foreshortening, between the stent body and tubular member.

Polymers can be selected to provide desirable mechanical or chemical properties. For example, highly elongatable or elastic polymers rather than rigid polymers can be used to allow relative movement between a stent body and cover. In some embodiments, a layer of the polymer can have an elongation at break of at least 500%, at least 800%, at least 900%, or at least 1000%. A layer of the polymer can have a tensile modulus of at least 10,000 psi, at least 50,000 psi, or at least 75,000 psi. A layer of the polymer has a tensile strength of at least 2,500 psi, at least 5,000 psi, at least 7,500 psi, or at least 10,000 psi.

In some embodiments, the polymer includes or is formed of a butyric acid derivative polymer, e.g., poly-4-hydroxybutyrate, poly-4-hydroxybutyrate, or poly-(3-hydroxybutyrate-co-4-hydroxybutyrate). The butyric acid derivative polymer film may have a tensile strength of at least about 7,500 psi, a tensile modulus of about 10,000 psi, and an elongation at break of about 1,000%. Exemplary butyric acid derivative polymers are available from Tepha, Inc. of Cambridge, Mass. and include TephELAST$_{31}$ and TephaFLEX. Such butyric acid derivative polymers can provide better elongation and strength than polytetrafluorethylene while also providing an amount of lubricity.

The polymer can include a urethane alone or in combination with one or more additional polymers, e.g., as a copolymer. Exemplary urethanes include, e.g., biodegradable urethanes such as bone cement, polyurethane, dispersions and/or emulsions including aqueous dispersions and/or emulsions such as NeoRez R-985 (aliphatic polycarbonate diol), NeoRez R-986 (aliphatic polycarbonate diol) from Astra-Zeneca, W830/048 (polycarbonate backbone), W830/092 (modified polycarbonate backbone), W830/140 (polycarbonate backbone) and W830/256 (polycarbonate backbone), from Industrial Copolymer Ltd., Bayhydrol 121 (anionic dispersion of an aliphatic polycarbonate urethane polymer in water and n-methyl-2-pyrrolidone with a tensile strength of 6,700 psi and an elongation at break of 150%) and Bayhydrol 123 (anionic dispersion of an aliphatic polycarbonate urethane polymer in water and n-methyl-2-pyrrolidone with a tensile strength of 6,000 psi and an elongation at break of 320%) from Miles Inc. (Bayer AG).

In some embodiments, the polymer includes both urethane and silicone, e.g., a polyurethane/silicon copolymer. Such polymers can be highly compressible and exhibit elongations before break of 400% or more. Polyurethane/silicon copolymers tend to provide good adherence to the endoprosthesis. Exemplary silicone-polyurethane copolymers include the Elast-Eon series of polymers, e.g., Elast-Eon 2A, Elast-Eon 2D, Elast-Eon 3A, Elast-Eon 3LH and Elast-Eon HF polymers, available from Aortech of Victoria, Australia.

Other exemplary polymers include, e.g., biocompatible, non-porous or semi-porous polymer matrices made of a fluoropolymer, e.g., polytetrafluoroethylene (PTFE) or expanded PTFE, polyethylene, natural nylon, aqueous acrylic, silicone, polyester, polylactic acid, polyamino acid, polyorthoester, polyphosphate ester, polypropylene, polyester, or combinations thereof.

In some embodiments, polymer layer 101 includes a biodegradable polymer. Exemplary biodegradable polymers include natural nylon, polysaccharides such as for example, methyl cellulose, hydroxymethyl cellulose, hydroxyethyl cellulose, hydroxypropyl cellulose, hydroxypropylmethyl cellulose, hydroxpropylethyl cellulose, sodium carboxymethyl cellulose, hyaluronic acid, chondroitin sulfate, chitosan, dextran, xanthan, gellan, alginic acid, jota carrageenan; polypeptides such as for example, collagen, gelatin, elastin, albumin; and synthetic polymers such as for example, poly (vinyl alcohol), poly(lactic acid), polyglycolic acid, polycaprolactone, polyanhydride, ethylene vinyl acetate (EVA) their copolymers and mixtures thereof.

In some embodiments, degradation of polymer layer 101 is accompanied by the release of a pharmaceutically active compound, e.g., a therapeutic agent or drug. Polymers providing such a release function are described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. Release can also occur without substantial or any degradation of the polymer.

Polymer layers 101 can be formed by contacting a cover and stent body with a flowable or sprayable polymer, such as by dip coating or spray coating. Upon curing, the polymer provides functionality, e.g., securement, to the endoprosthesis. In some embodiments, significant portions, e.g., all of a length of an endoprosthesis are contacted with polymer. Subsequently, portions of the polymer are removed, e.g., by laser ablation after curing. Polymer can be removed quite selectively if desired. For example, a polymer that initially occludes fenestrations of a cover can later be removed from some or all of the fenestrations while leaving polymer surrounding the fenestrations. In other embodiments, portions of the cover or stent body are protected from contact with the polymer, e.g., by a mask or temporary coating.

Figure 3A:
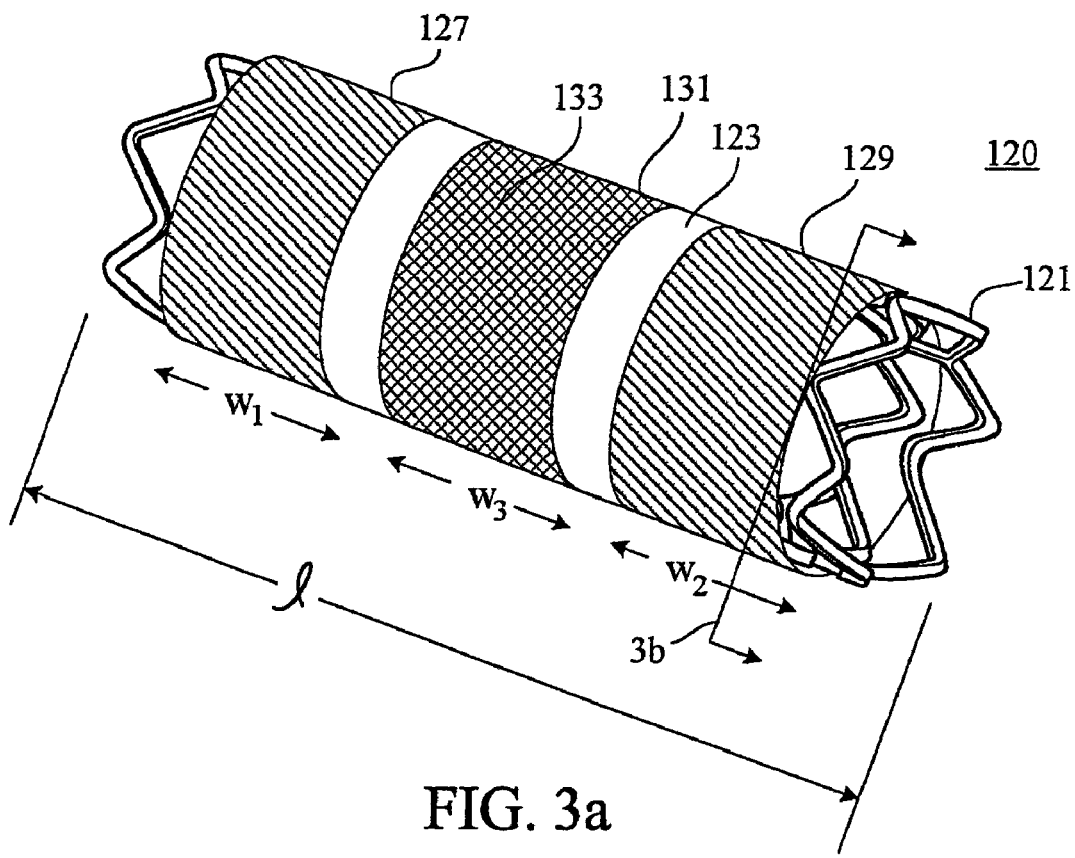
FIG. 3a is a perspective view of an endoprosthesis having a plurality of polymer layers.
Figure 3B:
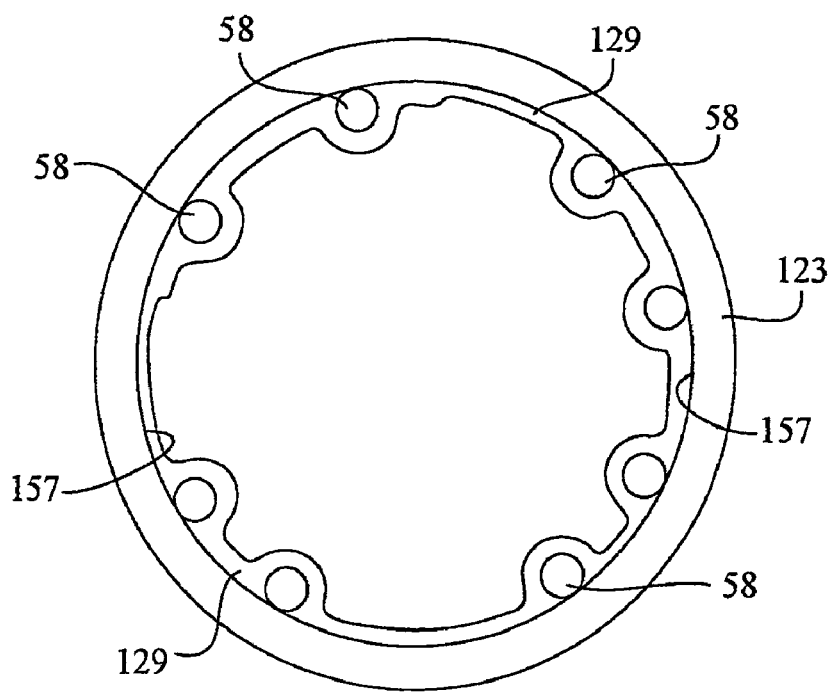

An endoprosthesis can include polymer layers configured differently from layers 101 to provide a securing function or other mechanical or biological functionalities. Referring to FIGS. 3a and 3b, an endoprosthesis 120 includes a stent body 121 surrounded by a cover 123. Two polymer end portions 127,129 and a polymer central portion 131 extend generally circumferentially without following particular elements of the stent body.

In some embodiments, end portions 127,129 are located within the cover. As seen in FIG. 3b polymer layer 129 provides a securing function by adhering to an inner surface 157 of the cover. Polyurethane-silicone copolymers exhibit suitable adhesion properties yet allow some freedom of movement between the stent body and cover to tolerate differential length changes upon compression-expansion. Framework members 58 of a stent body are enveloped by the polymer layer, which, in the cross-section shown, is not present on an external surface of the prosthesis. Film 123 does not include fenestrations in the cross section shown and may include no fenestrations at all. In alternative embodiments, the stent body surrounds the cover with the polymer layer enveloping portions of the stent body and adhering to an external surface of the cover.

In some embodiments, end portions 127,129 have a sufficient thickness and material properties to increase (or decrease) a radial expansive force exerted by the end portions of the endoprosthesis. As seen in FIG. 1a, end portions of a deployed endoprosthesis engage vessel walls to either side of an aneurysm. Radial force exerted by the ends of the endoprosthesis prevents movement along the vessel without damaging the vessel walls. Polymer layers 127,129 can cooperate with a stent body and cover to provide an appropriate level of radial force, such as by resisting expansion of the stent body.

Polymer end portions 127,129 have respective widths w1,w2, which may be at least about 10% of the length of the endoprosthesis, e.g., at least about 20%, at least about 40%, e.g., at least about 60% of the length. The widths w1,w2 may be different. One of the polymer end portions is not present in some embodiments. In some embodiments, polymer end portions are 25 μm thick or less, 20 μm thick or less, 15 μm thick or less, or 10 μm thick or less. The polymer can be formed of a plurality of individual layers, each having a thickness less than the total thickness of the polymer. For example, the polymer can be formed of a plurality of layers each having a thickness of 5 μm or less or 2 μm or less.

The central polymer portion 131 has a width w3 configured to straddle an aneurysm or other treatment site. In some embodiments, central polymer portion 131 provides a flow diversion or reduction function that can cooperate with fenestrations 133 of the cover. For example, polymer portion 131 may include a degradable polymer layer that initially occludes fenestrations 133 of the cover by an amount sufficient to further limit or prevent liquid, e.g., blood, from passing between an interior of the endoprosthesis (e.g., from within a vessel in which the endoprosthesis is disposed) and an exterior of the endoprosthesis (e.g., into an aneurysm adjacent the endoprosthesis). Because the polymer is degradable, the further limitation or occlusion of flow is temporary. The degradation of the layer, e.g., over weeks, months, or years, opens the occluded fenestrations 133 allowing increased passage of fluid through the previously occluded regions. The central polymer portion may also release drugs or other therapeutic agents. Of course, a polymer layer can be used to permanently occlude fenestrations of a cover.

In some embodiments, polymer end portions 127,129 are located external to cover 123 and include a topography or chemical properties configured to enhance long-term engagement of the endoprosthesis and the vessel walls adjacent the treatment site. For example, the topography of the outer surface of the polymer layers can include a plurality of pores having a size sufficient to enhance cell in-growth. The polymer releases compounds to enhance such growth. The central polymer portion may also release drugs or other therapeutic agents.

Figure 4:
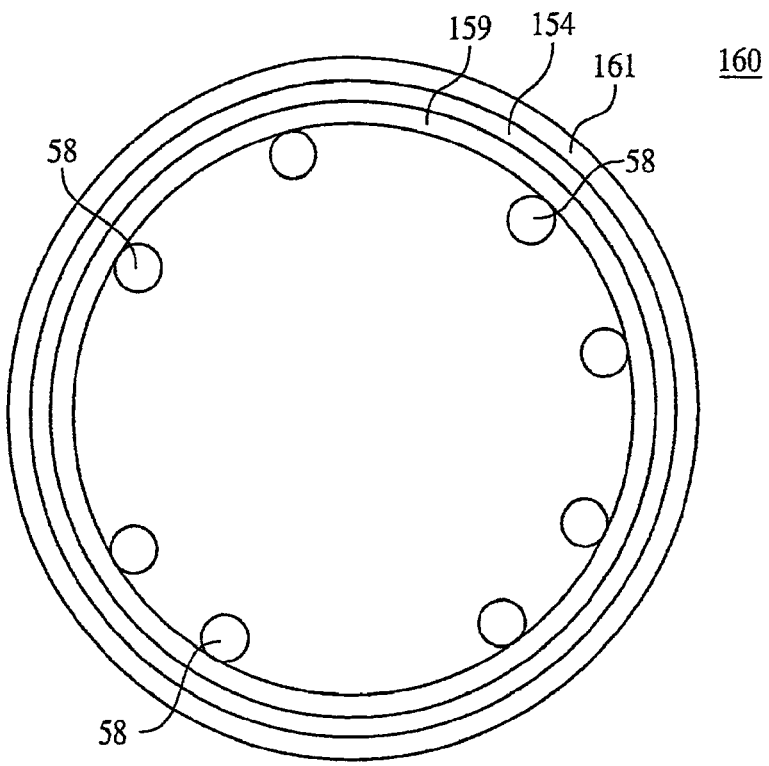
FIG. 4 is a cross-section through an endoprosthesis.

Referring to FIG. 4 an endoprosthesis 160 includes a composite cover comprising an interior polymer layer 159, a metallic film layer 154, and an exterior polymer layer 161. The composite cover surrounds a stent body with framework members 58. Layers 159,161 can be formed from a flowable composition of the polymer. In other embodiments, the metallic film is deposited, e.g., by vapor deposition, directly onto one of polymer layers 159 or 161. A polymer layer may itself be deposited from a vapor onto the metallic film. Alternative composites are also possible. For example, the layers may be reversed so that a polymer layer is sandwiched by two metallic layers.

Figure 5:
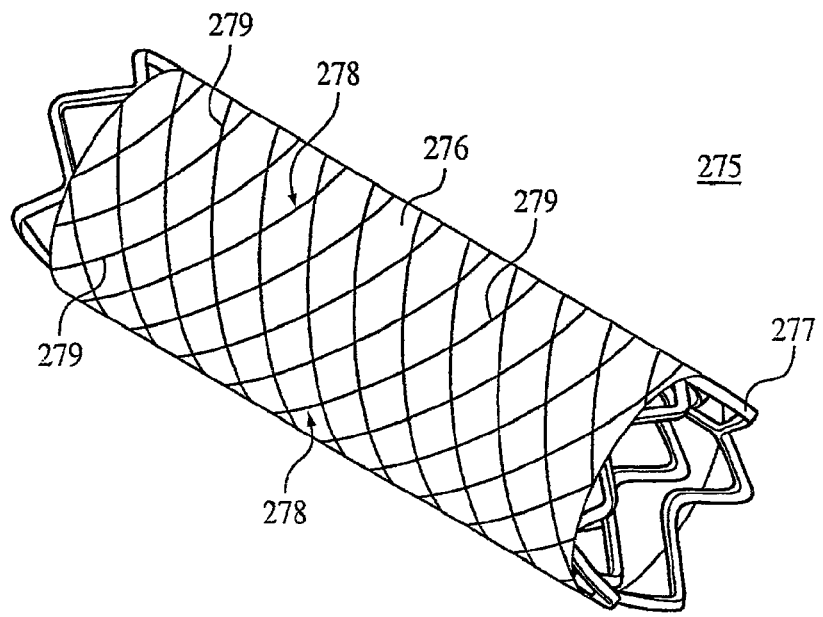
FIG. 5 is a perspective view of an endoprosthesis.

Referring to FIG. 5, an endoprosthesis 275 includes a patterned polymer layer 278, which modifies a radial force exerted by a stent body 277 and cover 154 of the endoprosthesis. Patterned polymer layer 278 is formed of a plurality of polymer strands 279 extending circumferentially with respect to the endoprosthesis 275. Each strand 279 defines a helix encircling an exterior of a cover 154. Strands defining opposed orientations cooperate to define a lattice structure of the patterned layer 278.

Strands 279 may be oriented fibers of a polymer having a high tensile modulus and tensile strength. In some embodiments, the strands are oriented fibers of a butyric acid derivative having a tensile modulus of at least 100,000 psi and a tensile strength of at least about 70,000 psi. Oriented fibers of TephaFLEX available from Tepha, Inc. are exemplary. The oriented fibers can guide and constrain radial expansion of the endoprosthesis. In such embodiments, the maximum expanded diameter of the deployed endoprosthesis may be less than a diameter attained in the absence of pattern 278.

Strands 279 may be formed of a polymer having a highly compressible polymer having a high elongation before break. Urethane-silicone copolymers such as from the Elast-Eon series of polymers from Aortech can provide such properties. For example, a polymer Elast-Eon 3LH from Aortech has a tensile modulus of about 1,000 psi and an elongation before break of about 650%. Such highly compressible and elongatable polymers can contribute positively to a radial force exerted by the endoprosthesis.

The polymer pattern 278 can be formed by spin coating strands 278 such as by extruding a polymer through a nozzle and rotating the endoprosthesis with respect to the nozzle. The extruded strands 279 typically have a thickness of about equal to or less than cover 154. In some embodiments, strands 279 may have a diameter of about 10 μm or less, e.g., about 2 μm or less.

The polymer bands can have a thickness less than that of the tubular member. For example, the polymer bands can be about 50% of a thickness of a thin film of the tubular member.

Although pattern 278 is shown disposed about an entire length of cover 154, a central portion, e.g., at least a central 30%, 40%, 60%, 80%, or 90% of the endoprosthesis 275 may lack a polymer pattern sufficient to substantially modify a radial expansive force of the endoprosthesis. For example, a central portion of the endoprosthesis can include a polymer that contributes to other properties, e.g., lubricity, fenestration occlusion, or therapeutic agent delivery without substantially altering a radial expansive force of the endoprosthesis.

Figure 6:
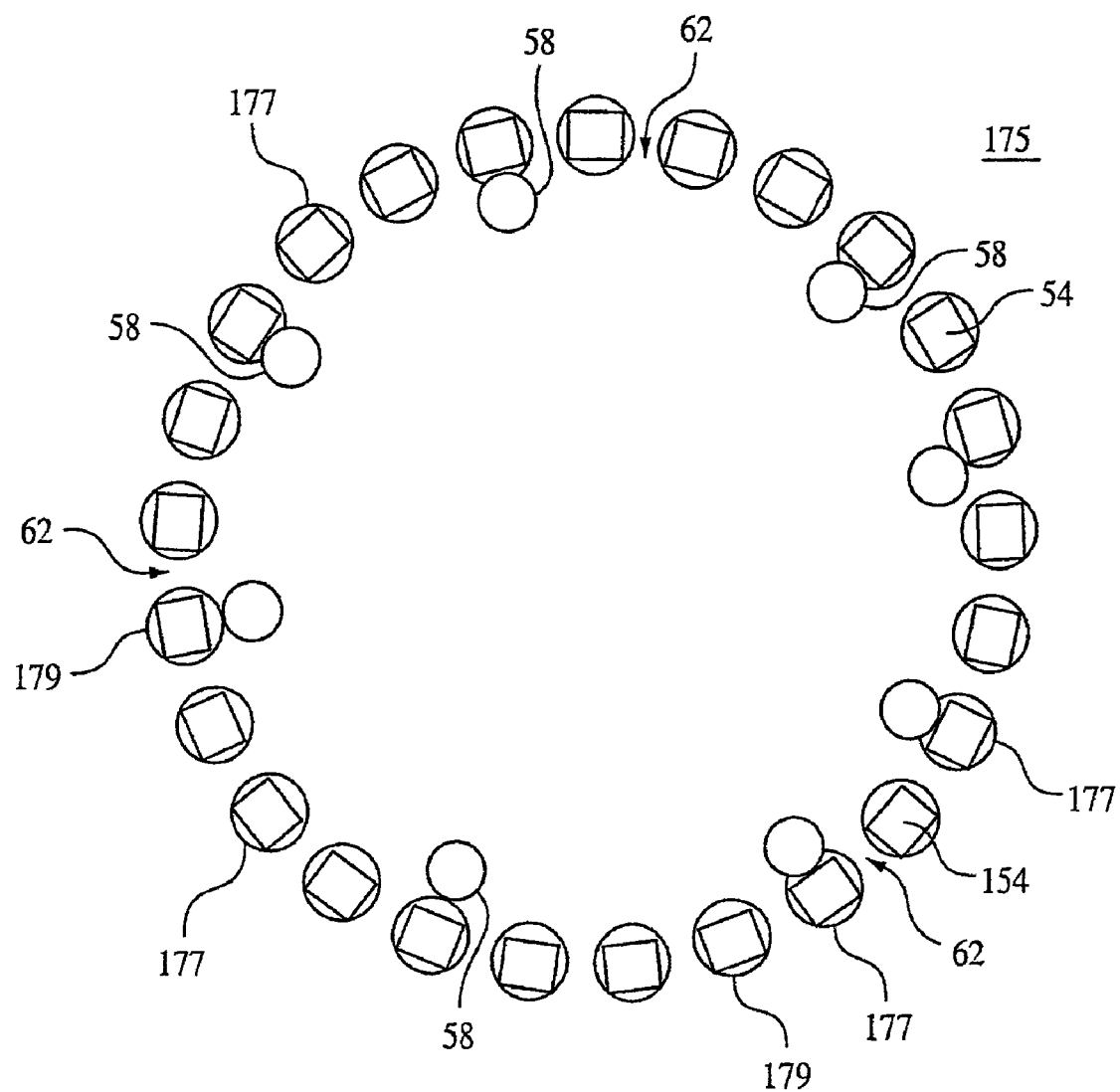
FIG. 6 is a cross-section of an endoprosthesis.

Referring to FIG. 6, an endoprosthesis 175 seen in cross-section includes a stent body having framework members 58 and cover 54 enveloped by a polymer layer 177, which provides a smoother outer surface than an untreated, deposited metallic film. Compared to the untreated film, the polymer layer 177 can have a smoother topography, an increased lubricity, a lower surface energy, improved mechanical properties, e.g., improved stretchiness or tear resistance, or combination thereof. For example, outer portions 179 of the cover 54 exhibit a lower coefficient of friction when translated with respect to the inner surface of a sheath used to deploy the endoprosthesis. Hence, during deployment, less force is required to begin withdrawing the sheath from the radially compressed endoprosthesis. In the embodiment shown, fenestrations 62 of cover 54 are not occluded by layer 177, which has a smaller thickness than the cover. For example, layer 177 may have a thickness of a few microns or less.

Figure 7A:
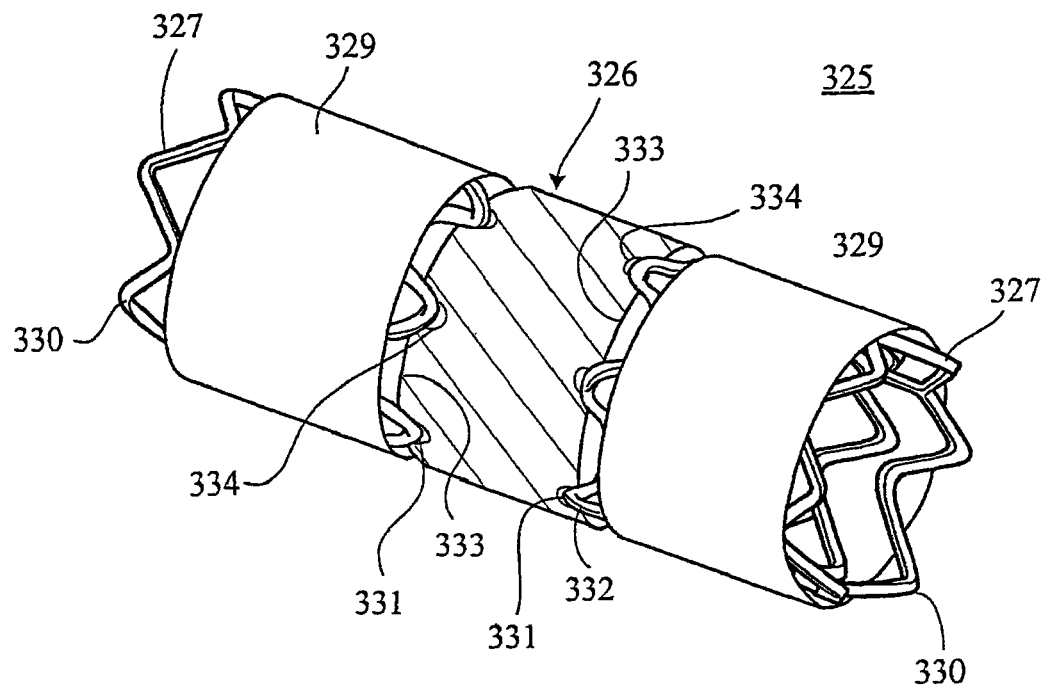
FIG. 7a is an endoprosthesis having a degradable central portion.

Referring to FIG. 7a, an endoprosthesis 325 includes a biodegradable center portion 326, which can be used to temporarily occlude a site, e.g., an aneurysm, and later provide increasing flow or access to the site. Center portion 326 is disposed between two stent bodies 327 each having an outer end 330 and an inner end 331. Center portion 326 is secured between inner ends 331 of stent bodies 327. For example, inner ends 331 may include struts 332, which crimp about outer edges 333 of center portion 326. Radiopaque markers 334 define boundaries between inner ends 331 of stent bodies 327 and outer edges 333 of center portion 326.

Figure 7B:
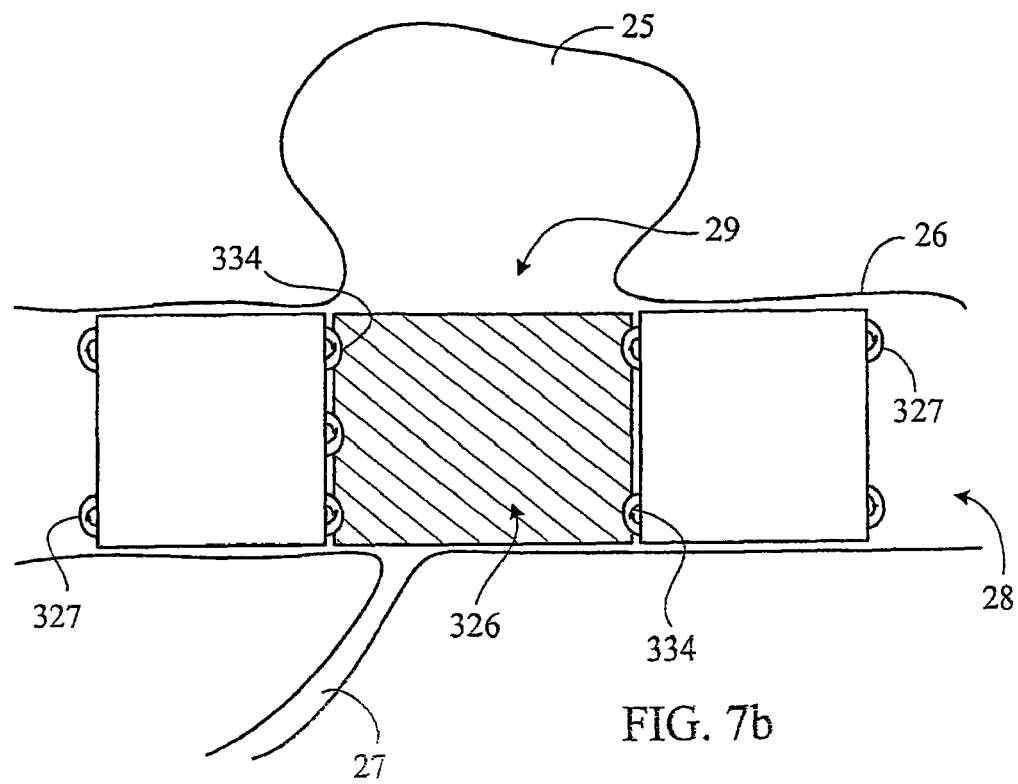
FIG. 7b is the endoprosthesis of FIG. 7a deployed in a body passage with the central portion not yet degraded.

With reference to FIG. 7b, endoprosthesis 325 is deployed within a body passage, e.g., to a site of aneurysm 25. Markers 334 are visualized to position endoprosthesis 325 so that outer edges 333 of center portion 326 straddle opening 29 of aneurysm 25. The endoprosthesis is deployed as described above. Upon deployment, center portion 326 limits or prevents flow of blood between interior 28 of vessel 26 and aneurysm 25. Center portion 326 may include fenestrations so as not to restrict blood flow entirely. Hence, center portion 326 may allow flow between feeder 27 (if present) and vessel interior 28.

Over time following deployment, e.g., weeks, months, or even several years, center portion 326 degrades. In embodiments, the entirety of center portion 326 is composed of degradable material so that, upon complete degradation, only endoprosthesis portions upstream and downstream of markers 334 remain intact within vessel 26. The degradation provides increased flow between interior 28 of vessel 26 and sites, e.g., aneurysm 25, once occluded by center portion 326. Degradation of the central portion 326 can be accompanied by release of a pharmaceutically active compound.

In other embodiments, center portion 326 includes a biodegradable portion and another portion, which is either not biodegradable or has a significantly different degradation lifetime. For example, prosthesis 325 may include markers that allow circumferential positioning of the prosthesis with respect to aneurysm 25 and feeder vessel 27. A first portion of center portion 326 has a short degradation lifetime and is oriented to face feeder 27. A second portion of center portion has a longer degradation lifetime as is oriented to face aneurysm 25. Accordingly, prosthesis 325 can provide both rapid reestablishment of flow between a vessel weakened by an aneurysm and a vessel branching therefrom and long-term flow reduction with respect to the aneurysm itself.

Stent bodies 327 may, e.g., be surrounded by, tubular members 329, which, except for being shorter, may have properties of tubular members discussed herein. For example, the tubular members 329 may each include a thin film, such as a metallic film. In some embodiments, tubular members 329 increase a surface area of endoprosthesis 325 as compared to a surface area if the members were not present. The increased surface area can enhance the longitudinal fixation of the prosthesis with respect to vessel 26, especially upon degradation of center portion 326. Tubular members 329 can include coating that enhances cell in growth with respect to the members. In some embodiments, a metallic film extends between and connects tubular members 329. In some embodiments, tubular members 329 are only connected by center portion 326.

In some embodiments, the endoprosthesis lacks one or both of the stent bodies. Instead, the outer edges 333 of center portion 326 can each be initially secured to a tubular member 329 having sufficient thickness, e.g., at least 35 μm, to exert a securing radial force. The center portion and tubular members 329 are joined by, e.g., crimping. Upon degradation of the center portion, all that may remain is the tubular members and markers, if present. In some embodiments, the tubular members are connected by struts or portions of the tubular member that extend across center portion 326.

Figure 8A:
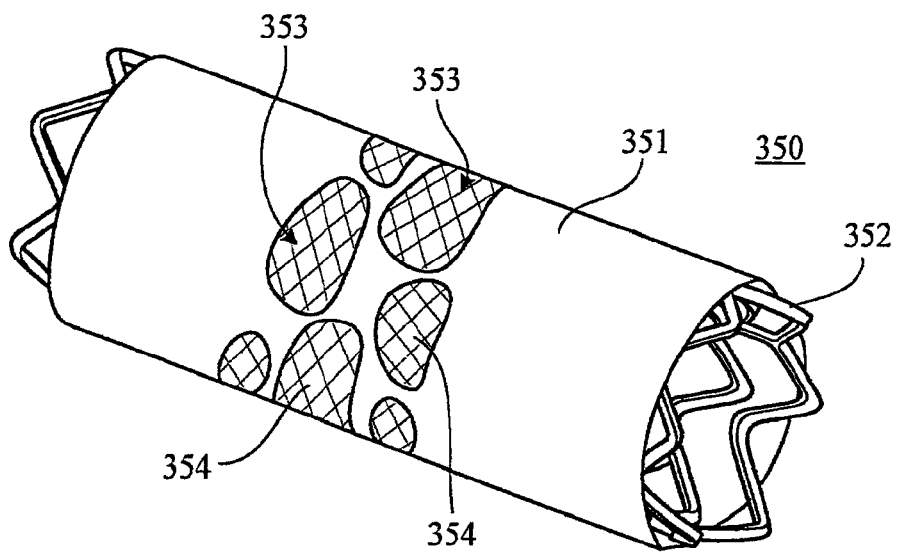
FIG. 8a is an endoprosthesis with degradable portions.
Figure 8B:
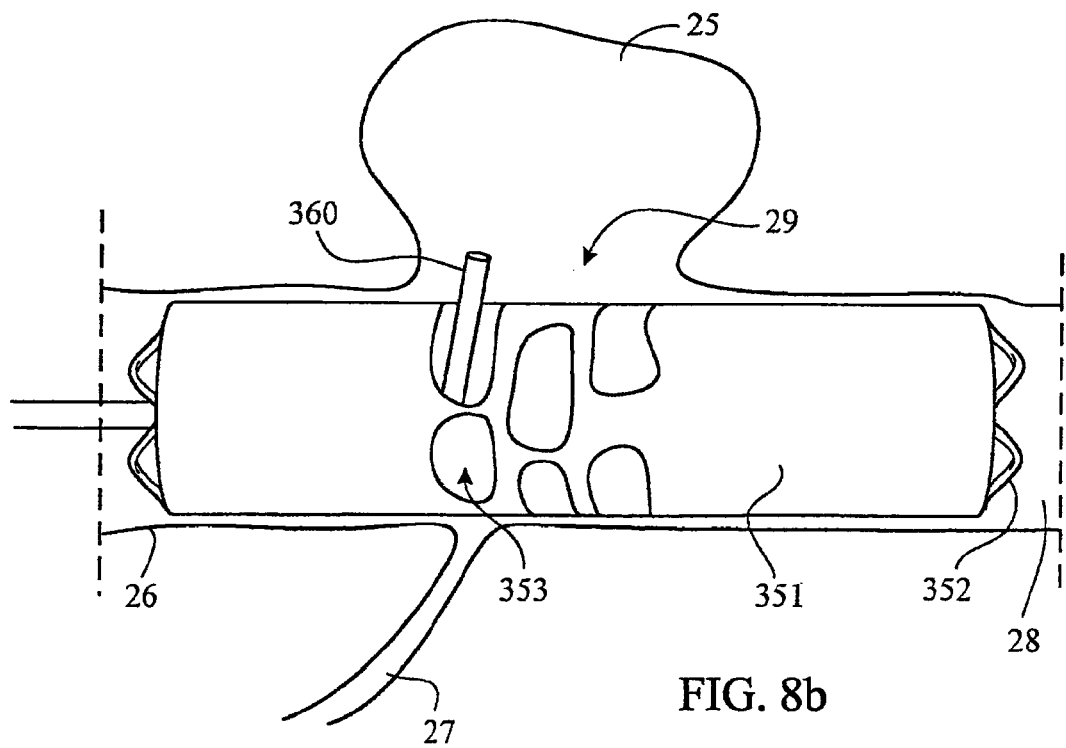
FIG. 8b is the endoprosthesis of FIG. 8a deployed in a body passage. A medical instrument is inserted through a degraded portion of the endoprosthesis.

Referring to FIGS. 8a and 8b, an endoprosthesis 350 includes a tubular member 351 having plurality of fenestrations 353, which are initially occluded by a degradable layer 354. In use, endoprosthesis 350 is deployed so that occluded fenestrations 353 are aligned with a treatment site, e.g., aneurysm 25. Initially, degradable layer 354 obstructs passage between interior 28 of vessel 26 and locations external thereto, e.g., aneurysm 25. Subsequent to deployment, layer 354 degrades and may open fenestrations 353 entirely. Fenestrations 353 can be large enough to provide passage for an instrument, e.g., a catheter, to extend from interior 28 of vessel 26 at least to opening 29 of aneurysm 25 and perhaps even further therein (FIG. 8b). For example, fenestrations 353 can be at least large enough to provide passage for a 1.7 french catheter 360. The fenestrations 353 can have an unobstructed area of 2 mm2 or more. In some embodiments, degradable layer 354 itself includes fenestrations, which may allow for some flow therethrough even when the layer is not yet degraded.

In some embodiments, endoprosthesis 325 includes an array of fenestrations 353 as shown. In other embodiments, the endoprosthesis includes only a few or even one circumferential fenestration. The endoprosthesis can include markers that are indicative of a circumferential orientation of the fenestrations. Hence, the fenestrations 353 can be aligned not only longitudinally with respect to aneurysm 25 but circumferentially with respect to opening 29 or feeder 27.

Figure 9A:
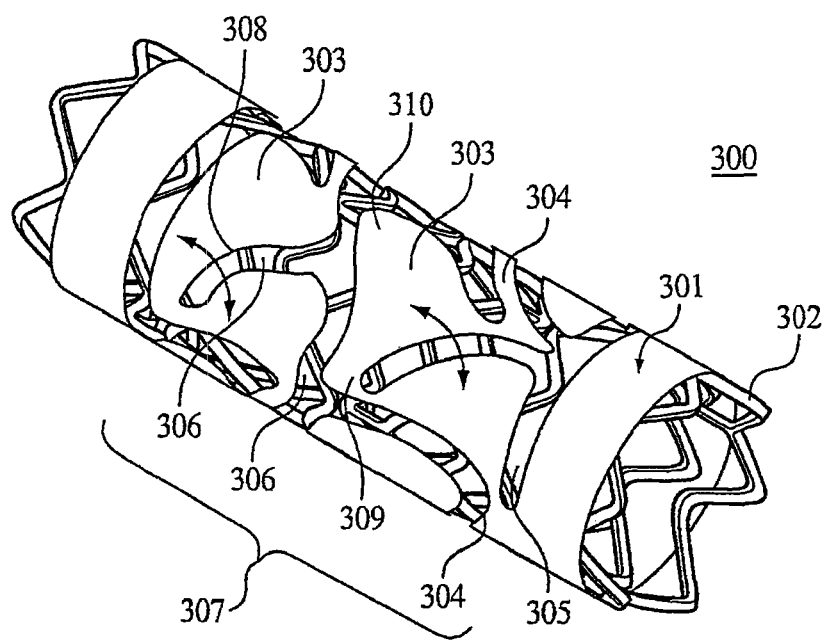
FIG. 9a is an endoprosthesis having a cover having a plurality of movable plates.

Referring to FIG. 9a, an endoprosthesis 300 includes a tubular member 301 having a plurality of plates 303, which spread apart upon radial expansion of the endoprosthesis. Because of the expansion, tubular member 301 can be radially compressed to a small diameter and then radially expand upon deployment to provide a substantially greater surface area than in the absence of spreading plates 303. Accordingly, endoprosthesis 300 can be delivered within a radially compact delivery device yet conform to the wall of a relatively larger diameter vessel upon deployment.

A central portion 307 of tubular member 301 includes a plurality of plates 303 connected by struts 304. A stent body 302 supports plates 303 and end portions of the tubular member. Adjacent plates 303 are separated by gaps 306 through which framework members 305 of stent body 302 can be seen. In other embodiments, the stent body does not extend between opposite ends of the endoprosthesis. Instead, two independent stent bodies provide a radial outward force to secure the prosthesis in a vessel.

Figure 9B:
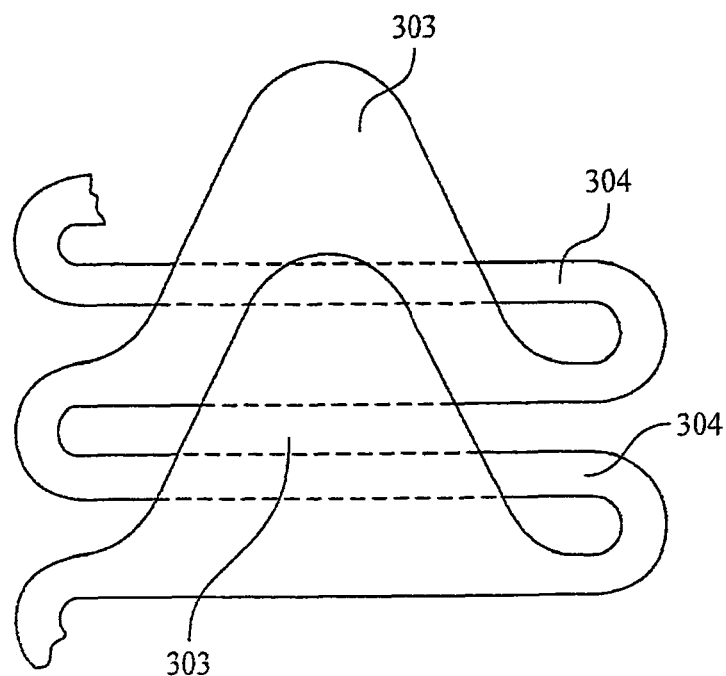
Figure 9C:
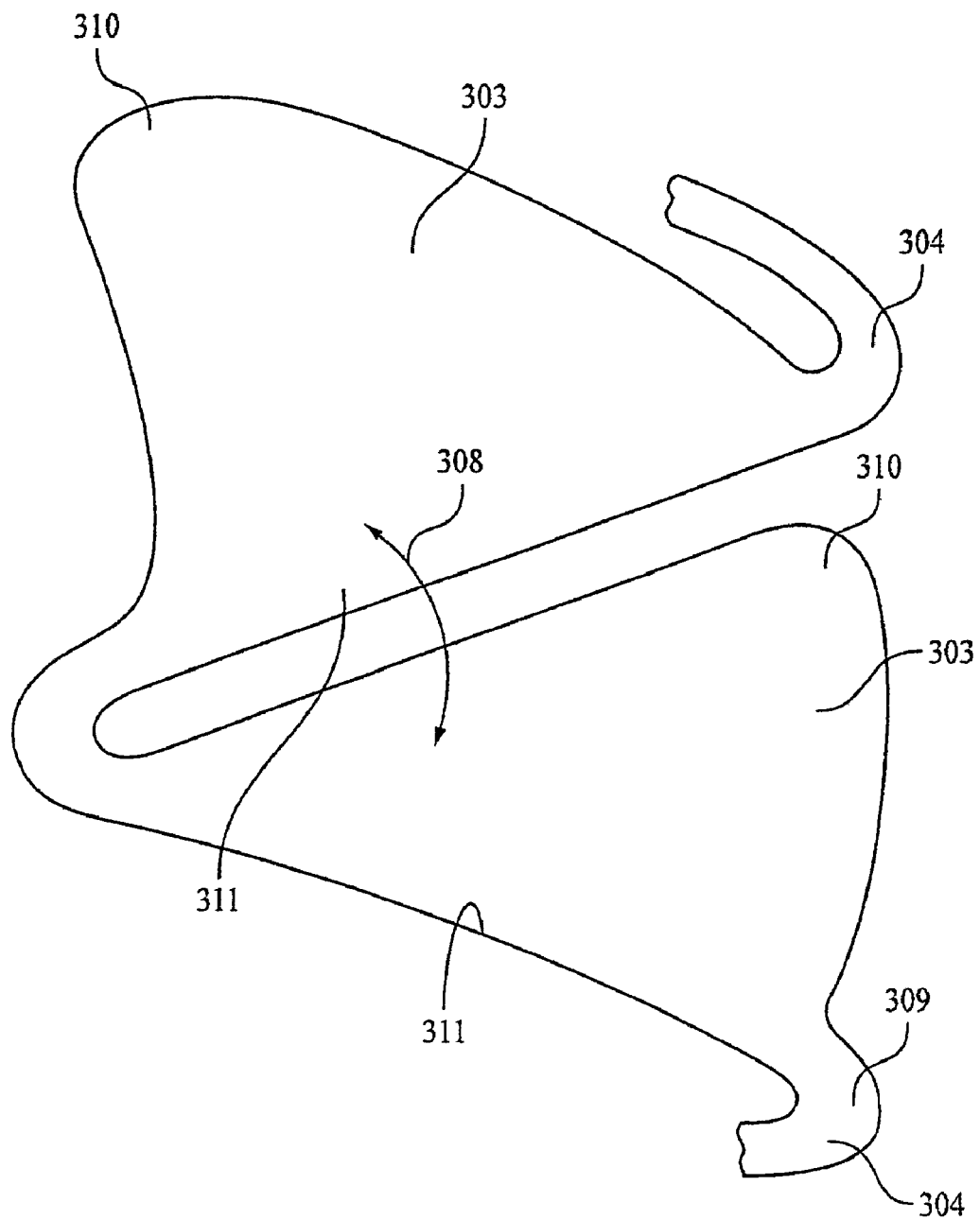

Referring also to FIG. 9b, adjacent plates 303 overlap when endoprosthesis 300 is radially compressed as for delivery along a blood vessel to an aneurysm site. Referring to FIG. 9c, plates 303 spread apart upon radial expansion increasing the effective surface area of central portion 307. Arrows 308 illustrate generally the relative movement of adjacent plates 303. Because plates 303 overlap when radially compressed and spread apart when radially expanded, central portion 307 tubular member 301 can define a greater surface area than would otherwise be possible without significantly changing the surface area of plates 303 themselves.

In some embodiments, at least 10%, at least 25%, at least 35%, at least 50%, or at least 70% of plates 303 are overlapped in the radially compressed state. Hence, the apparent surface area of endoprosthesis 300 can be significantly larger in the expanded state than in the radially compressed state. In some embodiments, 30% or less, 20%, or less, e.g., 10% or less of plates are overlapped in the radially expanded state. Some degree of overlap between plates can help limit a tendency of a plate to flex radially outwards or inwards in response to blood flow internal to or external to the deployed prosthesis. For example, a tip 310 of a plate can overlap or be overlapped by a base 311 of another plate (FIG. 9c).

A deposited metallic film can contribute desirable mechanical properties to plates and struts of the cover. For example, tubular member 300 can include a thin film, e.g., metallic film comprising nickel, titanium, and, optionally, a strength additive, e.g., chromium. An amount of strength additive may vary in different portions of the film. In some embodiments, elbows 309 include a different amount of strength additive than plates 303.

Plates and struts including a deposited metallic film can be formed with minimal thickness, e.g., about 50 microns or less, e.g., about 4 to about 35 microns. Struts 304 can include elbows 309 defining significant bends, e.g., 130° or more, 150° or more, or 180° or more. Elbows 309 can have a composition and/or cross-section different from plates 303. In some embodiments, elbows have a circular or oval cross-section whereas as plates 303 are substantially planar.

Figure 10A:
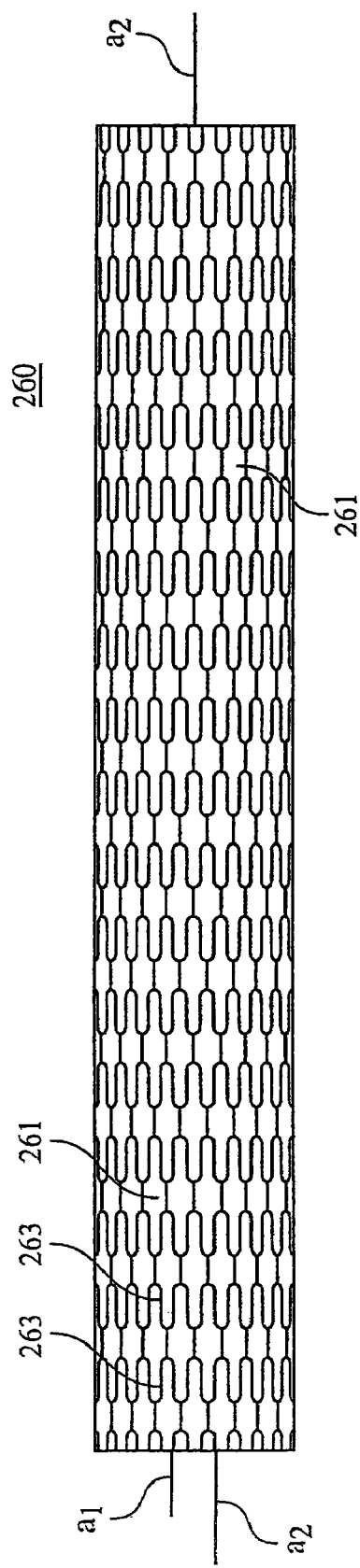
FIG. 10a is cover with a metallic film defining fenestrations configured to have minimal stress in a radially compressed state.

Referring to FIG. 10a, a metallic film 260 useful as a cover of an endoprosthesis includes a plurality of fenestrations 261 having minimal stress when radially compressed within a delivery device. Minimizing stress in the radially compressed state can reduce or prevent deformation, e.g., warping or kinking, of the film. Upon radial expansion, the fenestrations 261 may experience a relatively greater stress than an alternative fenestration configuration. However, because forces experienced by the radially expanded film tend to be more uniform, the film can tolerate radial expansion without deformation.

Figure 10B:
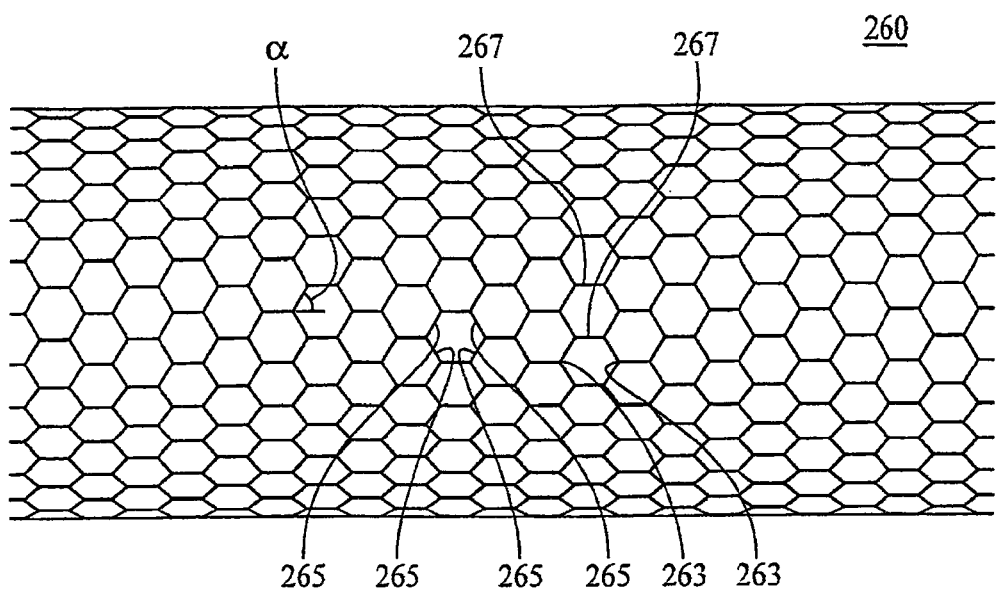
FIG. 10b illustrates the cover of FIG. 10a in a state of radial compression about midway between the radially compressed state of FIG. 10a and a fully expanded state.

In a relatively unexpanded state (FIG. 10a), each fenestration 261 includes a plurality of parallel walls extending along a major fenestration axis a1, which is parallel to a longitudinal axis a2 of an endoprosthesis that would receive the film 260 as a cover. Ends 263 of each fenestration are arcuate. Upon partial radial expansion (FIG. 10b), interior walls 265 adjacent the ends 263 spread apart defining a non-parallel angle α with the longitudinal axis a2. A pair of centrally located walls 267 remain parallel to one another. Accordingly, each fenestration 261 assumes a hexagon shape.

Figure 10C:
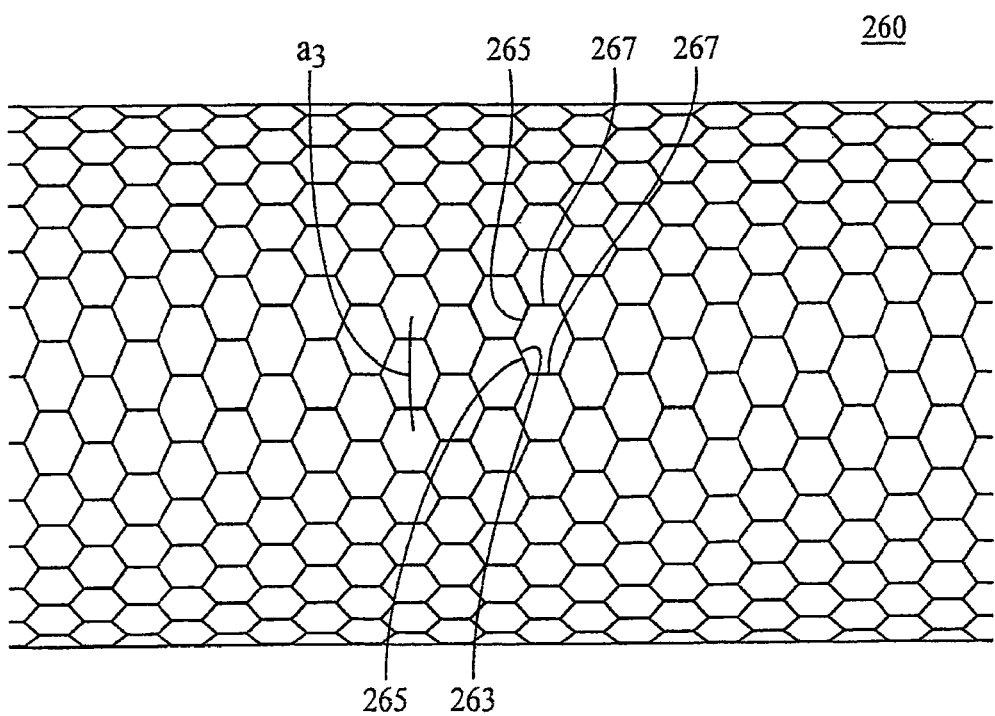
FIG. 10c illustrates the cover of FIG. 10a in a state of radial expansion about that assumed in a body passage.

In a fully expanded state (FIG. 10c), e.g., at vessel size, walls 265 spread further apart and each fenestration 261 assumes an elongated hexagon having a major axis a3 aligned with a circumferential axis of the endoprosthesis. Walls 267 remain parallel to one another despite the circumferential elongation.

Figure 11:
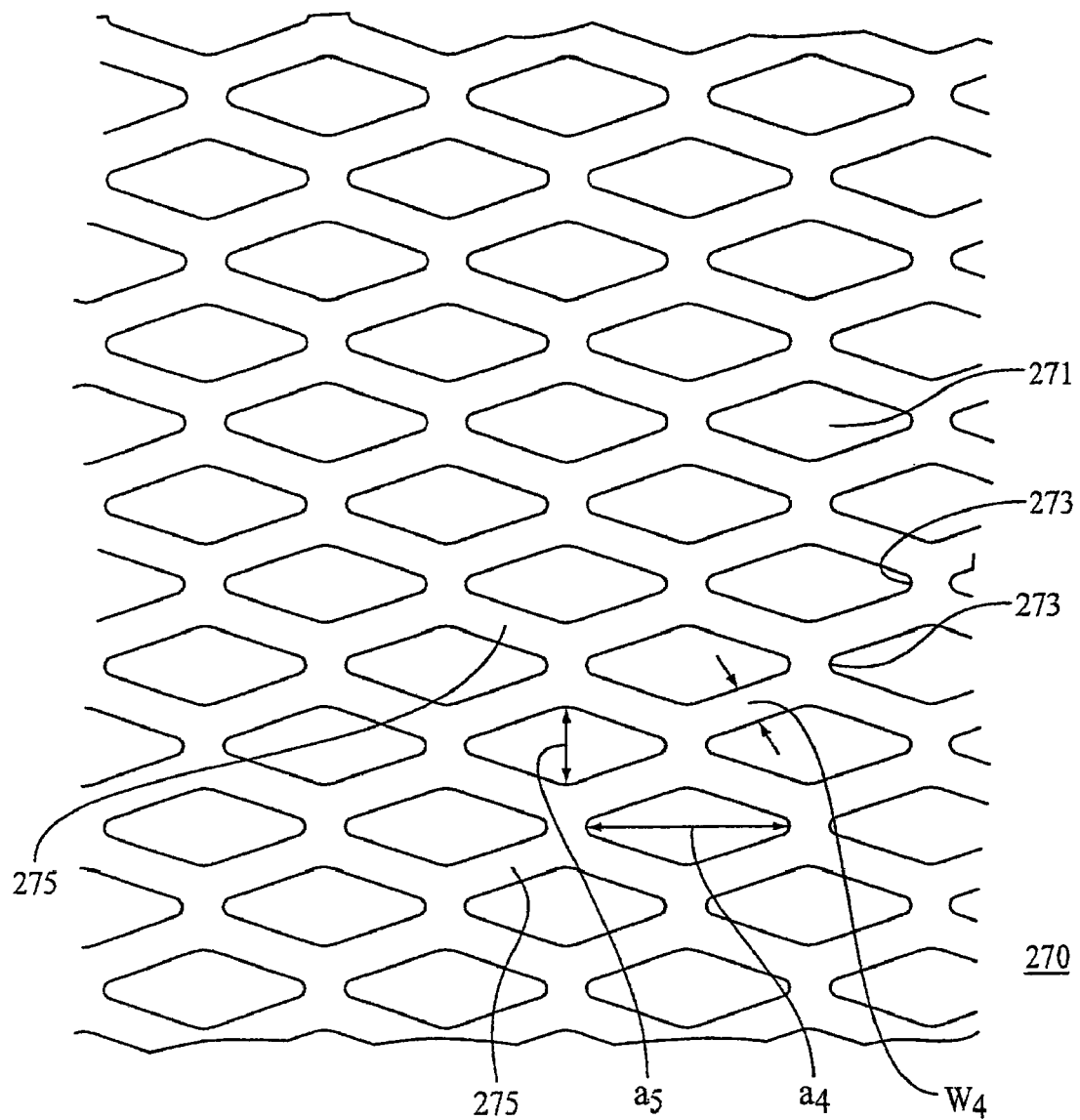
FIG. 11 is a cover with a metallic film defining fenestrations configured to have minimal stress in a radially expanded state within a body passage.

Referring to FIG. 11, a metallic film 270 useful as a cover of an endoprosthesis includes a plurality of struts 275, which define fenestrations 271 having minimal stress when radially expanded within a body passage, e.g., a vessel. In an unexpanded state, as shown, fenestrations 271 have a diamond shape defining a minor axis a5 and a major axis a4, which is aligned with a longitudinal axis of an endoprosthesis including the cover. A ratio (in the unexpanded state) of the major axis a4 to the minor axis a5 may be about 6 or less, about 5 or less, e.g., about 3 or less. A width w4 of metallic film struts 275 may be about 50 μm or less. A thickness of the film along a dimension normal to the film is less than the thickness of the struts and may be about 15 μm or less.

In addition to selecting a fenestration configuration that minimizes stress at a particular radial dimension, a cover can be shape set at a selected radial dimension. This shape set radial dimension may or may not match the radial dimension that minimizes stress of the fenestrations. A film can be shape set by, for example, setting the film at the selected radial dimension and heating the film to, e.g., about 500° C. In some embodiments, the film is shape set at a diameter about the same as or somewhat larger than an inner diameter of a delivery device sheath that surrounds the tubular member during implantation. In another embodiment, the film is shape set at a diameter about the same as or somewhat smaller than the inner diameter of a body passage to receive an expanded endoprosthesis. A stent body used with the cover may also be shape set to a selected radial dimension. A ratio of the shape set diameter of the cover 54 to the expanded diameter of stent body 52 in the absence of tubular member 54 may be about 1 or less, about 0.95 or less, or about 0.9 or less.

In other embodiments, a deposited metallic thin film and one or more polymer layers are useable as an endoprosthesis without a supporting stent. For example, an endoprosthesis without a supporting stent can include a deposited thin film formed of a selected alloy and one or more polymer layers to enhance radial and/or longitudinal strength. In embodiments, the deposited metallic film is in the shape of a tube of substantially uniform thickness. The metallic film can include a pattern of polymer layers or strands.

In the embodiment shown, endoprosthesis 100 has a generally tubular shape. In some embodiments, however, the endoprosthesis (or stent body 52 or tubular member 54 individually) has or includes other shapes such as conical, oblate, and branched. The endoprosthesis may have a closed end to form, e.g., a basket shape. Thin films, discussed above, composed of Ni—Ti-strength additive alloys and/or with modified microstructures, can be used in other applications. Examples include baskets, filters, catheters, guidewires, and medical balloons, such as an angioplasty balloon.

Other examples of endoprostheses including a thin film as well as related systems and methods are described in U.S. provisional patent application No. 60/549,287, filed Mar. 2, 2004, which application is incorporated herein by reference.

An endoprosthesis may include a cover disposed externally to a framework as shown and/or internally of a framework. Endoprostheses having a cover including, e.g., a deposited thin film, disposed internally of a framework are described in U.S. patent application Ser. No. 11/025,464, titled MEDICAL DEVICES INCLUDING METALLIC FILMS AND METHODS FOR MAKING SAME, and filed concurrently herewith, which application is incorporated herein by reference.

An endoprosthesis may include features to enhance a flexibility of the endoprosthesis as described in U.S. patent application Ser. No. 11/025,158, titled MEDICAL DEVICES INCLUDING METALLIC FILMS AND METHODS FOR MAKING SAME, and filed Dec. 29, 2004, which application is incorporated herein by reference.

The composition and/or fabrication method of a deposited thin film of an endoprosthesis may include features that enhance a strength or toughness of the film as described in U.S. patent application Ser. No. 11/025,860, titled MEDICAL DEVICES INCLUDING METALLIC FILMS AND METHODS FOR MAKING SAME, and filed Dec. 29, 2004, which application is incorporated herein by reference.

An endoprosthesis may include one or more filaments, e.g., wires, adapted to enhance mechanical properties of a deposited thin film as described in U.S. patent application Ser. No. 11/025,684, titled MEDICAL DEVICES INCLUDING METALLIC FILMS AND METHODS FOR MAKING SAME, and filed Dec. 29, 2004, which application is incorporated herein by reference.

Methods for loading an endoprosthesis into a delivery device and systems for delivering an endoprosthesis to a treatment site are described in U.S. patent application Ser. No. 11/025,660, titled MEDICAL DEVICES INCLUDING METALLIC FILMS AND METHODS FOR LOADING AND DEPLOYING SAME, filed Dec. 29, 2004, which application is incorporated herein by reference.

All publications, references, applications, and patents referred to herein are incorporated by reference in their entirety.

Other embodiments are within the claims.

What is claimed is:

1. An endoprosthesis, comprising:
a generally tubular metallic film having a plurality of plates; and
a framework, at least a portion of which is covered by the generally tubular metallic film;
wherein at least 10% of the plurality of plates are overlapped in a radially compressed state.

2. The endoprosthesis of claim 1, wherein at least 25% of the plurality of plates are overlapped in a radially compressed state.

3. The endoprosthesis of claim 1, wherein at least 50% of the plurality of plates are overlapped in a radially compressed state.

4. The endoprosthesis of claim 1, wherein 30% or less of the plurality of plates are overlapped in a radially expanded state.

5. The endoprosthesis of claim 1, wherein 10% or less of the plurality of plates are overlapped in a radially expanded state.

6. The endoprosthesis of claim 1, wherein a tip of a plate overlaps with a base of an adjacent plate in the radially compressed state.

7. The endoprosthesis of claim 1, wherein the generally tubular metallic film has a surface area in a radially expanded state greater than a surface area in the radially compressed state.

8. The endoprosthesis of claim 1, wherein the plurality of plates are connected by a plurality of struts.

9. The endoprosthesis of claim 8, wherein each strut defines a bend of at least 130°.

10. The endoprosthesis of claim 1, wherein two adjacent plates in the generally tubular metallic film are separated by a gap in a radially expanded state.

11. The endoprosthesis of claim 1, wherein the generally tubular metallic film has a thickness of less than about 50 μm.

12. The endoprosthesis of claim 1, wherein the generally tubular metallic film comprises nickel, titanium, and optionally chromium.

13. The endoprosthesis of claim 12, wherein the generally tubular metallic film comprises nickel, titanium, and chromium, the plurality of plates are connected by a plurality of struts, the plurality of plates have an amount of chromium different than that of the plurality of struts.

14. An endoprosthesis, comprising:
a generally tubular metallic film having a plurality of plates;
wherein at least 10% of the plurality of plates are overlapped in a radially compressed state and a tip of a plate overlaps with a base of an adjacent plate in the radially compressed state.

15. The endoprosthesis of claim 14, further comprising a framework, at least a portion of which is covered by the generally tubular metallic film.

16. An endoprosthesis, comprising:
a generally tubular metallic film having a plurality of plates connected by a plurality of struts, each strut defining a bend of at least 130°;
wherein at least 10% of the plurality of plates are overlapped in a radially compressed state.

17. The endoprosthesis of claim 16, further comprising a framework, at least a portion of which is covered by the generally tubular metallic film.

18. An endoprosthesis, comprising:
a generally tubular metallic film having a plurality of plates;
wherein at least 10% of the plurality of plates are overlapped in a radially compressed state and two adjacent plates in the generally tubular metallic film are separated by a gap in a radially expanded state.

19. The endoprosthesis of claim 18, further comprising a framework, at least a portion of which is covered by the generally tubular metallic film.

20. An endoprosthesis, comprising:
a generally tubular metallic film having a plurality of plates;
wherein at least 10% of the plurality of plates are overlapped in a radially compressed state, the generally tubular metallic film comprises nickel, titanium, and chromium, the plurality of plates are connected by a plurality of struts, the plurality of plates have an amount of chromium different than that of the plurality of struts.

21. The endoprosthesis of claim 20, further comprising a framework, at least a portion of which is covered by the generally tubular metallic film.

* * * * *